United States Patent
Kuznia et al.

(10) Patent No.: US 8,724,944 B2
(45) Date of Patent: May 13, 2014

(54) FIBER OPTIC BI-DIRECTIONAL COUPLING LENS

(71) Applicants: Charles B. Kuznia, Encinitas, CA (US); Joseph F. Ahadian, San Marcos, CA (US); Richard T. Hagan, Mission Viejo, CA (US); Richard J. Pommer, Carlsbad, CA (US)

(72) Inventors: Charles B. Kuznia, Encinitas, CA (US); Joseph F. Ahadian, San Marcos, CA (US); Richard T. Hagan, Mission Viejo, CA (US); Richard J. Pommer, Carlsbad, CA (US)

(73) Assignee: Ultra Communications, Inc., Vista, CA (US)

( * ) Notice: Subject to any disclaimer, the term of this patent is extended or adjusted under 35 U.S.C. 154(b) by 0 days.

(21) Appl. No.: 13/692,366

(22) Filed: Dec. 3, 2012

(65) Prior Publication Data
US 2013/0094026 A1    Apr. 18, 2013

Related U.S. Application Data

(63) Continuation of application No. 12/617,021, filed on Nov. 12, 2009, now Pat. No. 8,335,411.

(60) Provisional application No. 60/113,298, filed on Nov. 11, 2008.

(51) Int. Cl.
| | |
|---|---|
| *G02B 6/32* | (2006.01) |
| *G02B 6/12* | (2006.01) |
| *G02B 6/26* | (2006.01) |
| *G02B 6/42* | (2006.01) |
| *G02B 6/293* | (2006.01) |

(52) U.S. Cl.
CPC .............. *G02B 6/4214* (2013.01); *G02B 6/4204* (2013.01); *G02B 6/4246* (2013.01); *G02B 6/2938* (2013.01)
USPC .................................. 385/33; 385/14; 385/47

(58) Field of Classification Search
None
See application file for complete search history.

(56) References Cited

U.S. PATENT DOCUMENTS

| | | | |
|---|---|---|---|
| 4,701,010 A | 10/1987 | Roberts | |
| 6,142,680 A | 11/2000 | Kikuchi | |
| 6,198,864 B1 | 3/2001 | Lemoff | |
| 6,201,908 B1 | 3/2001 | Grann | |
| 6,385,374 B2 | 5/2002 | Kropp | |
| 6,636,540 B2 * | 10/2003 | Uebbing | 372/36 |
| 6,636,658 B2 | 10/2003 | Goodman | |
| 7,349,602 B2 | 3/2008 | Panotopoulos | |
| 2001/0026663 A1 | 10/2001 | Kim | |
| 2002/0018635 A1 | 2/2002 | Hsieh | |
| 2003/0063844 A1 * | 4/2003 | Caracci et al. | 385/24 |
| 2003/0152336 A1 | 8/2003 | Gurevich | |
| 2004/0105161 A1 * | 6/2004 | Tatum et al. | 359/634 |
| 2005/0084217 A1 * | 4/2005 | Yoshimura et al. | 385/88 |
| 2008/0055589 A1 * | 3/2008 | Asami et al. | 356/73.1 |
| 2008/0226228 A1 * | 9/2008 | Tamura et al. | 385/33 |

FOREIGN PATENT DOCUMENTS

| | | |
|---|---|---|
| GB | 2162335 | 1/1986 |
| GB | 2162335 A * | 1/1986 |

* cited by examiner

*Primary Examiner* — Michelle R Connelly

(57) ABSTRACT

A component for coupling light bi-directionally between optical waveguides and optoelectronic devices is described. This component can be inexpensively manufactured and fits within the existing form-factor of fiber optic transceivers or transmitters, and has features for efficiently coupling laser light to a waveguide and light from the same waveguide to a detector. The described components can be formed as an array to operate within system that operation over parallel optical fibers. Applicability for these components is for optical time domain reflectometry, bi-directional optical communications, remote fiber sensing, and optical range finders.

13 Claims, 20 Drawing Sheets

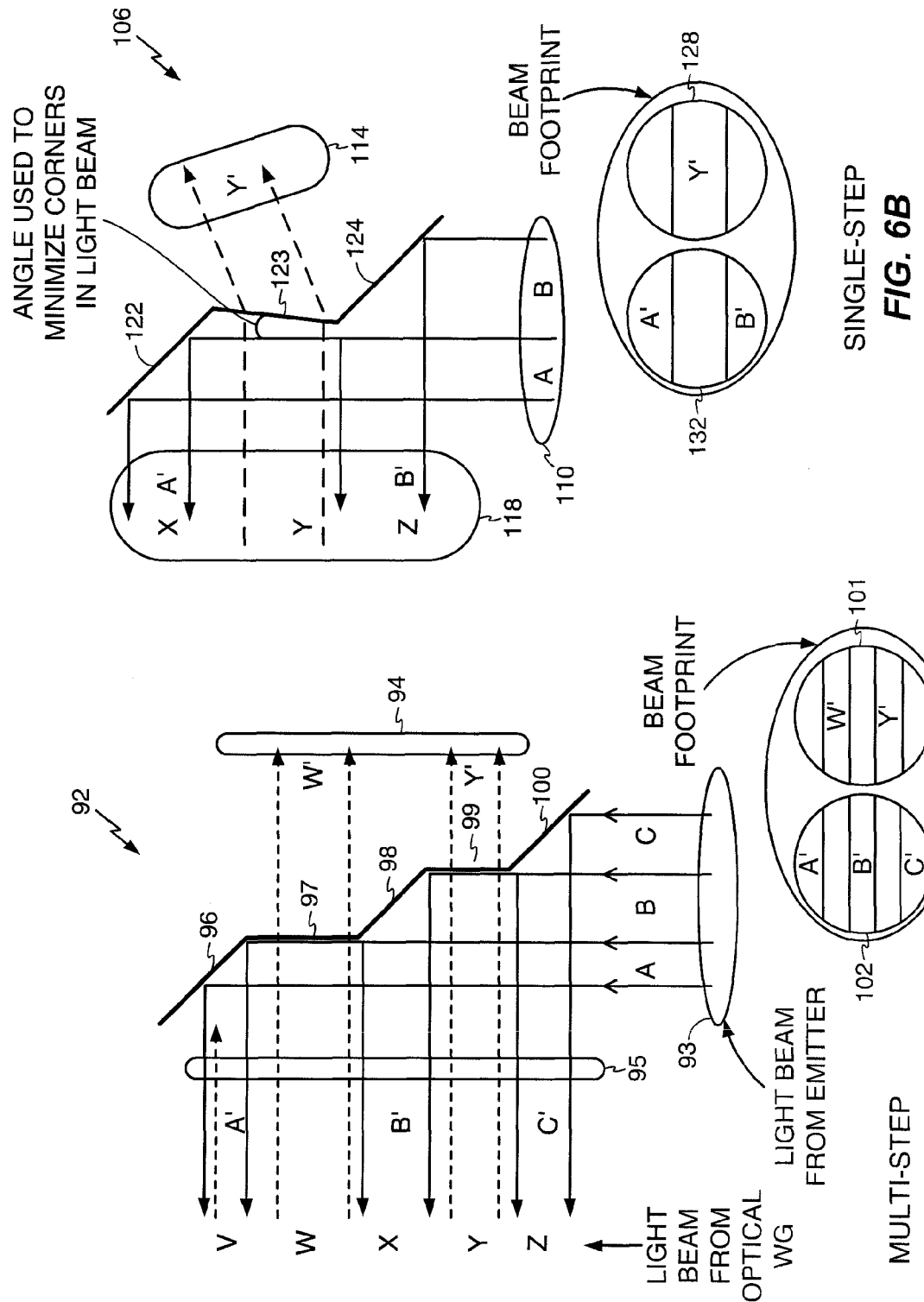

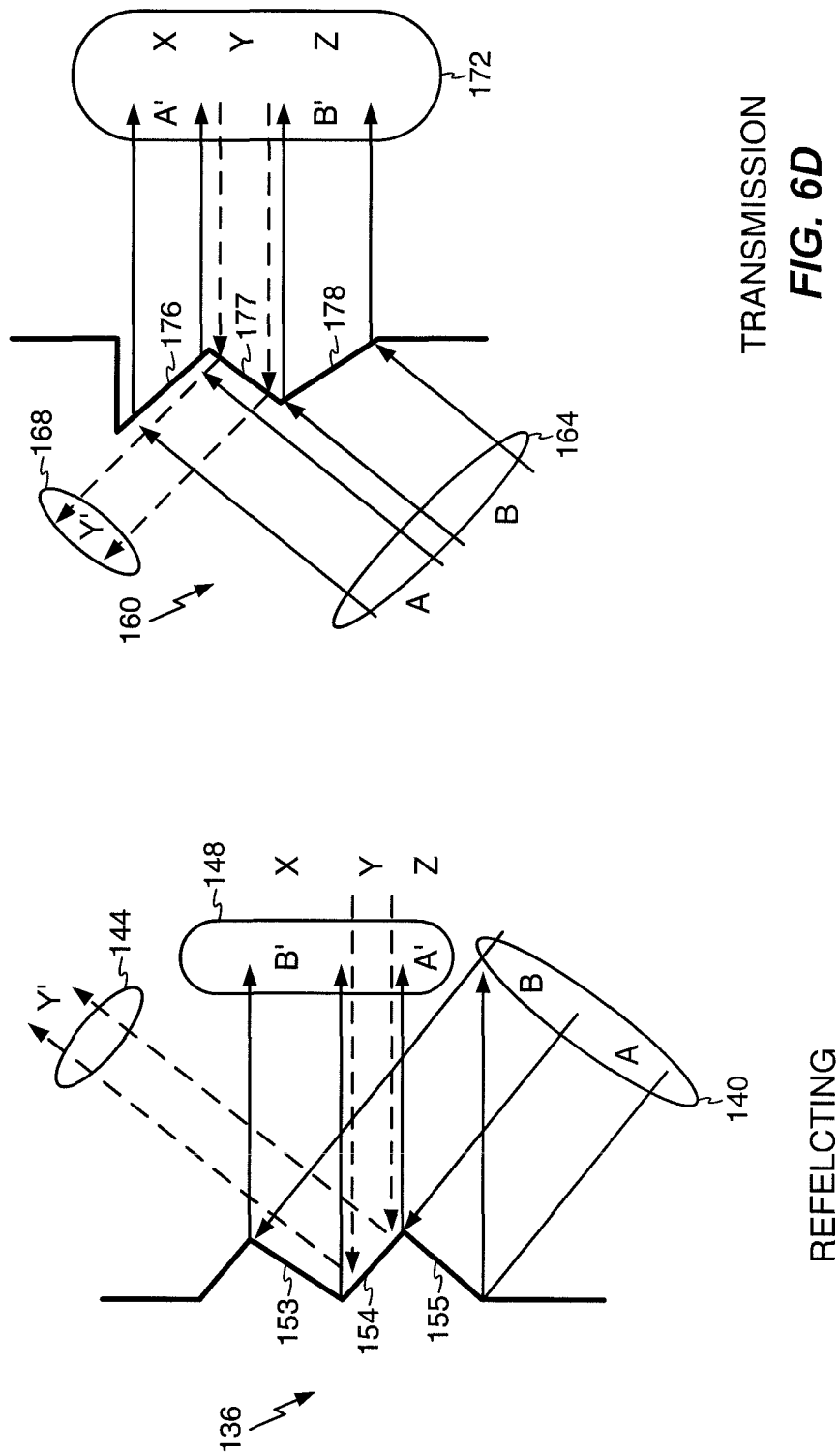

FOCUSED

ANNULAR

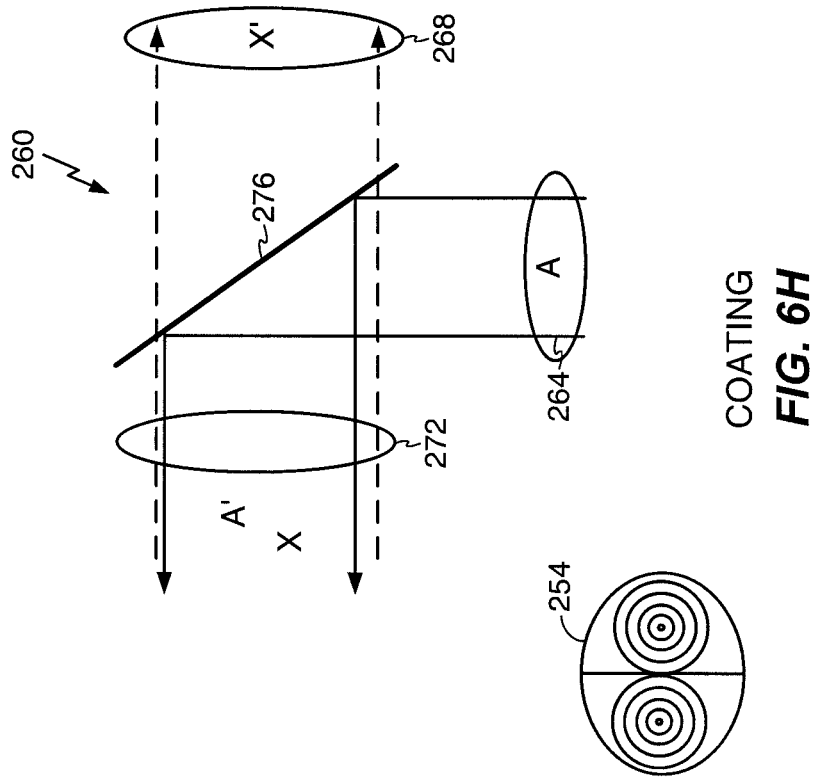
COATING FIG. 6H
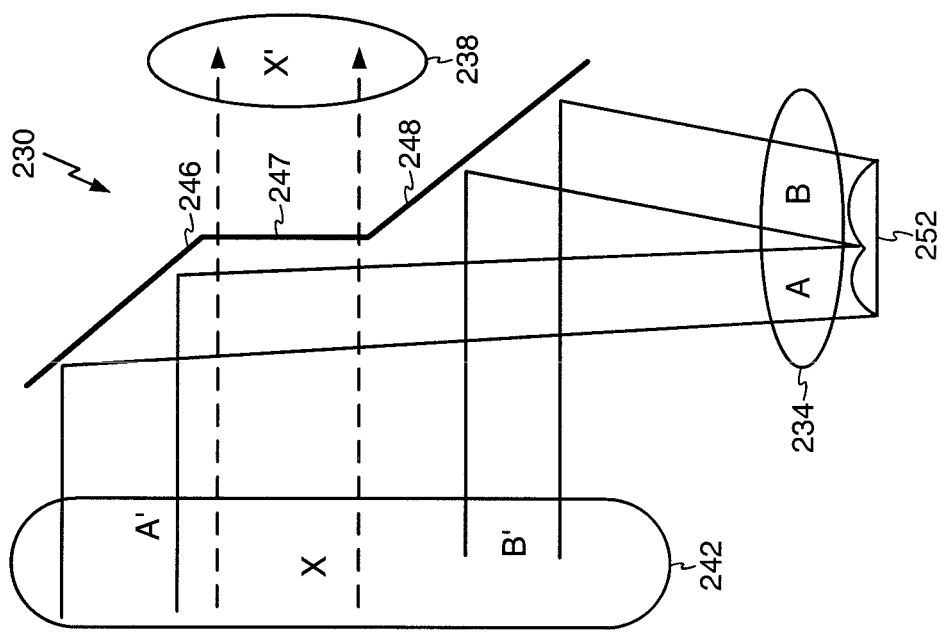
SPLIT BEAM FIG. 6G

FIBER OPTIC BI-DIRECTIONAL COUPLING LENS

CROSS-REFERENCE TO RELATED APPLICATION(S)

This application is a continuation of and claims the benefit of priority under 35 U.S.C. §120 to U.S. patent application Ser. No. 12/617,021, filed on Nov. 12, 2009, which claims the benefit of priority under 35 U.S.C. §119(e) to U.S. Provisional Patent Application No. 60/113,298, filed Nov. 11, 2008, the contents of each of which are incorporated by reference in their entireties.

FEDERALLY-SPONSORED RESEARCH AND DEVELOPMENT

This disclosure was made with Government support under N00014-06-M-0208 awarded by the United States Navy. The government may have certain rights.

FIELD

This disclosure relates to relates to devices that communicate over optical waveguides. More particularly, it relates to efficiently coupling laser light to a waveguide and light from the same waveguide to a detector.

BACKGROUND

Optical transmitters typically use a lens to couple light from a light emitting device into an optical waveguide, such as a fiber. In applications such as optical time domain reflectrometry (OTDR), optical frequency domain reflectrometry (OFDR) and bi-directional data communications (BIDI), it is necessary to couple light from the light emitter to the waveguide and couple light from this very same waveguide back to a light detecting device. These devices can be implemented in a manner to determine "breaks" in a fiber optic line.

However, such systems can be difficult to implement or require very specialized equipment. Therefore, there has been a long standing need in the optical testing community for methods and systems for addressing these and other difficulties in the electro-optical community.

SUMMARY

The foregoing needs are met, to a great extent, by the present disclosure, wherein in one aspect of the disclosed embodiments, a device for transmitting and reflecting light between a plurality of lenses is provided, comprising: a multi-sided transparent body having an indent therein; a light splitting surface formed integral to an interior end of the indent, capable of passing and reflecting split light; a first lens formed integral to a first side of the body; a second lens formed integral to a second side of the body, wherein the first lens and second lens are disposed in a reflected split light path of each other; a third lens formed integral to the first side of the body; and a reflector supporting angled surface formed integral to an exterior end of the indent, wherein a reflector positioned on the angled surface directs light from the third lens to the light splitting surface and directs light from the light splitting surface to the third lens.

In another aspect of the disclosed embodiments, a device for transmitting and reflecting light between a plurality of lenses is provided, comprising: a multi-sided transparent body, a light splitting surface formed integral to a first side of the body, capable of passing and reflecting split light; first lens formed integral to a second side of the body; a second lens formed integral to a third side of the body, wherein the first lens and second lens are disposed in a reflected split light path of each other; wherein the light splitting surface passes light from the second lens onto a non-integral lens.

In another aspect of the disclosed embodiments, a device for transmitting and reflecting light between a plurality of lenses is provided, comprising: a light splitting surface capable of passing and reflecting split light based on an angle of incidence; a first lens and light emitter combination in a first path, at an angle to the light splitting surface; a second lens and waveguide combination in a second path, substantially on an axis of the light splitting surface; and a third lens and light detector combination in a third path, at another angle to the light splitting surface, wherein light from the first lens and light emitter combination is bent towards the second lens and waveguide combination, and light from the second lens and waveguide combination is bent towards the third lens and light detector combination.

In yet another aspect of the disclosed embodiments, a device for transmitting and reflecting light between a plurality of lenses is provided, comprising: a multi-sided transparent body having a first and second indent therein; a light splitting surface formed integral to an interior end of the first indent, capable of passing and reflecting split light; a transparent standoff that fits into the second indent; a first lens and a third lens, each formed integral to a device side of the standoff; a second lens formed integral to a first side of the body, wherein the first lens and second lens are disposed in a reflected split light path of each other; and a reflector supporting angled surface formed integral to an exterior end of the first indent, wherein a reflector positioned on the angled surface directs light from the third lens to the light splitting surface and directs light from the light splitting surface to the third lens.

In yet another aspect of the disclosed embodiments, a device for transmitting and reflecting light between a plurality of lenses is provided, comprising: a multi-sided transparent body having a first and second indent therein; a light splitting surface formed integral to an interior end of the first indent, capable of passing and reflecting split light; a first and third lens formed integral to an interior end of the second indent; a second lens formed integral to a first side of the body, wherein the first lens and second lens are disposed in a passed split light path of each other; and a reflective angled surface formed integral to a second side of the body, wherein light from the second lens to the light splitting surface is reflected to the reflective angled surface and reflected to the third lens.

In yet another aspect of the disclosed embodiments, a method for transmitting and reflecting light between a plurality of lenses is provided, comprising: forming a multi-sided transparent body having an indent therein; forming a light splitting surface integral to an interior end of the indent, capable of passing and reflecting split light; forming a first lens integral to a first side of the body; forming a second lens integral to a second side of the body, wherein the first lens and second lens are disposed in a reflected split light path of each other; forming a third lens integral to the first side of the body; forming a reflector supporting angled surface integral to an exterior end of the indent, wherein a reflector positioned on the angled surface directs light from the third lens to the light splitting surface and directs light from the light splitting surface to the third lens; illuminating the first lens with a beam of light, wherein light is reflected from the light splitting surface to a waveguide disposed in line with the second lens; and receiving light from the waveguide that is passed through the light splitting surface and reflected to the third lens to a light detector.

In another aspect of the disclosed embodiments, a method for transmitting and reflecting light between a plurality of lenses is provided, comprising: forming a multi-sided transparent body: forming a light splitting surface integral a first side of the body, capable of passing and reflecting split light; forming first lens integral to a second side of the body; forming a second lens integral to a third side of the body, wherein the first lens and second lens are disposed in a reflected split light path of each other, wherein the light splitting surface passes light from the second lens onto a non-integral lens; illuminating the first lens with a beam of light, wherein light is reflected from the light splitting surface to a waveguide disposed in line with the second lens; and receiving light from the waveguide that is passed through the light splitting surface and reflected to the non-integral lens to a light detector.

In yet another aspect of the disclosed embodiments, a method for transmitting and reflecting light between a plurality of lenses is provided, comprising: forming a light splitting surface capable of passing and reflecting split light based on an angle of incidence; aligning a first lens and light emitter combination in a first path, at an angle to the light splitting surface; aligning a second lens and waveguide combination in a second path, substantially on an axis of the light splitting surface; and aligning a third lens and light detector combination in a third path, at another angle to the light splitting surface, wherein light from the first lens and light emitter combination is bent towards the second lens and waveguide combination, and light from the second lens and waveguide combination is bent towards the third lens and light detector combination; illuminating the first lens with a beam of light, wherein light is reflected from the light splitting surface to a waveguide disposed in line with the second lens; and receiving light from the waveguide that is passed through the light splitting surface and reflected to the non-integral lens to a light detector.

In yet another aspect of the disclosed embodiments, a method for transmitting and reflecting light between a plurality of lenses is provided, comprising: forming a multi-sided transparent body having a first and second indent therein; forming a light splitting surface integral to an interior end of the first indent, capable of passing and reflecting split light; forming a transparent standoff that fits into the second indent; forming a first and third lens formed to a device side of the standoff; forming a second lens integral to a first side of the body, wherein the first lens and second lens are disposed in a reflected split light path of each other; forming a reflector supporting angled surface integral to an exterior end of the first indent, wherein a reflector positioned on the angled surface directs light from the third lens to the light splitting surface and directs light from the light splitting surface to the third lens; illuminating the first lens with a beam of light, wherein light is reflected from the light splitting surface to a waveguide disposed in line with the second lens; and receiving light from the waveguide that is passed through the light splitting surface and reflected to the non-integral lens to a light detector.

In yet another aspect of the disclosed embodiments, a method for transmitting and reflecting light between a plurality of lenses provided, comprising: forming a multi-sided transparent body having a first and second indent therein; forming a light splitting surface integral to an interior end of the first indent, capable of passing and reflecting split light; forming a first and third lens integral to an interior end of the second indent; forming a second lens integral to a first side of the body, wherein the first lens and second lens are disposed in a passed split light path of each other; forming a reflective angled surface integral to a second side of the body, wherein light from the second lens to the light splitting surface is reflected to the reflective angled surface and reflected to the third lens; illuminating the first lens with a beam of light, wherein light is reflected from the light splitting surface to a waveguide disposed in line with the second lens; and receiving light from the waveguide that is passed through the light splitting surface and reflected to the non-integral lens to a light detector.

In another aspect of the disclosed embodiments, a device for transmitting and reflecting light between a plurality of lenses is provided, comprising: means for light path manipulation having an indent therein; means for splitting light integral to an interior end of the indent, capable of passing and reflecting split light; first means for focusing light formed integral to a first side of the means for light path manipulation; first means for focusing light formed integral to a second side of the means for light path manipulation, wherein the first and second means for focusing light are disposed in a reflected split light path of each other; third means for focusing light formed integral to the first side of the means for light path manipulation; and means for supporting a reflector integral to an exterior end of the indent, wherein a reflector positioned on the means for supporting directs light from the third means for focusing light to the means for splitting light and directs light from the means for splitting light to the third means for focusing light.

BRIEF DESCRIPTION OF THE DRAWINGS

FIGS. 6A-I are diagrams of showing exemplary methods of forming a light splitting surface.

DETAILED DESCRIPTION

Introduction

Figure 1:
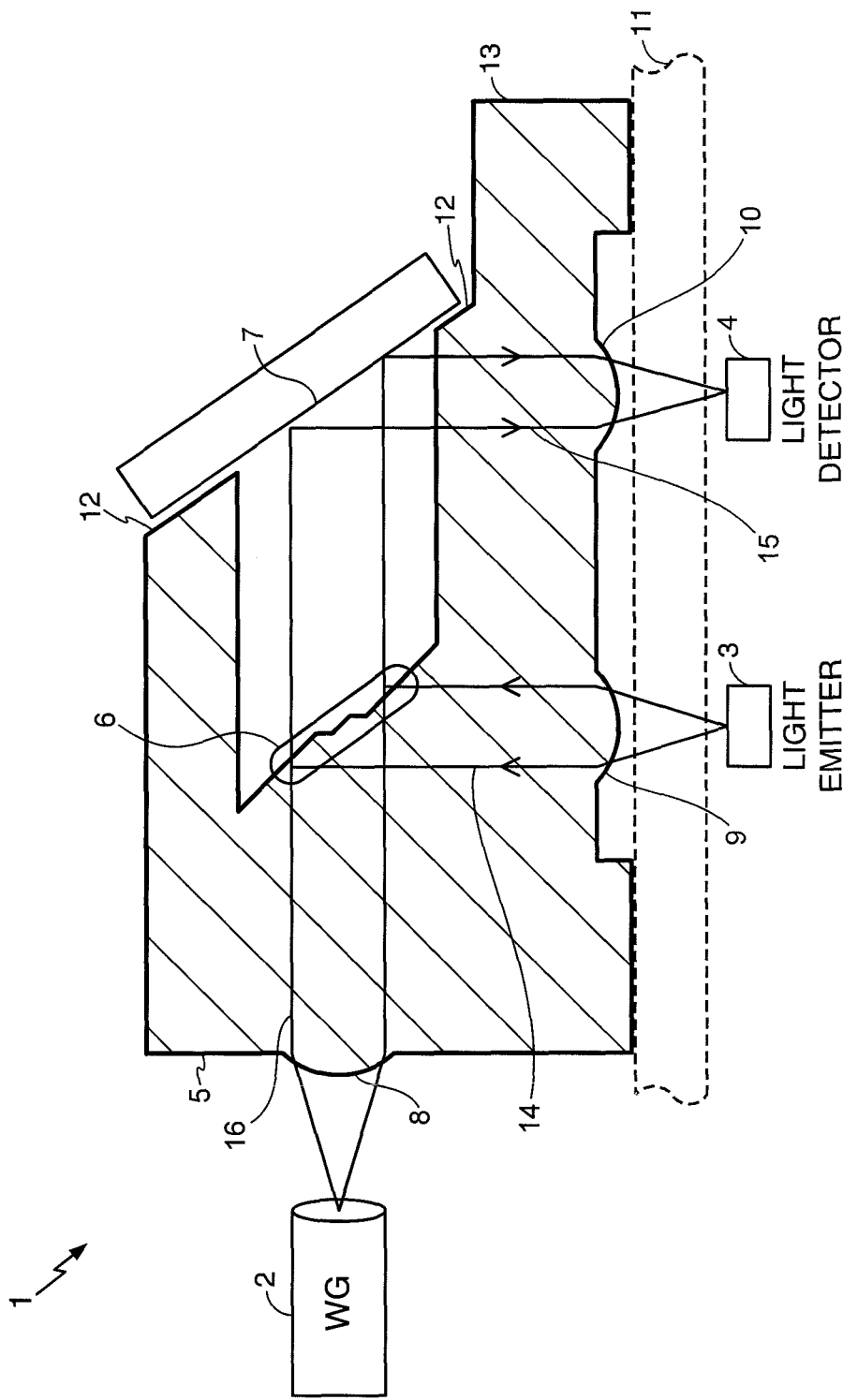
FIG. 1 is a diagram of an embodiment showing coupling light between a light emitter and waveguide using a first surface turn light toward the waveguide, and using this first surface to pass light from the waveguide to a second surface reflector. The second surface reflector turns the light toward a detector.

OTDR is a well known method of finding the location of discontinuities within the length of an optical waveguide. If a portion of a waveguide is damaged or broken, this section will reflect a portion of the light back to the light source. An OTDR system typically operates by transmitting a short pulse of light down the waveguide and measuring the time delay of the light pulse reflected from the discontinuity. The time delay is proportional to the distance traveled within the waveguide and thereby the location of the discontinuity is determined OTDR is performed today with a specialized piece of test equipment. To perform OTDR, the user disconnects one end of the optical link (either on the transmitter or receiver end) and inserts the test equipment. The OTDR test equipment then indicates the locations of discontinuities in the fiber path. Since fiber optical connections have traditionally been implemented for long distance communications, OTDR equipment is designed to measure lengths of fiber of 1000 meters or more. These applications are sometimes called fiber to the home, wide area networks or local area networks. Over these long spans, the acceptable accuracy of OTDR equipment, in terms of resolving the location of a fiber discontinuity, is not less than 1 meter.

Rather than use a specialized piece of test equipment, another method of performing OTDR is to implement the function within the optical transmitter. This would allow automated testing of the fiber link for discontinuities without disconnecting the link. This is highly desirable for fiber optic networks that have the transmitters and receivers in locations that are not easily accessible by a technician with OTDR test equipment. For example, military aircraft can have tens to hundreds of fiber links that move data among sensors, displays and data processing units. The optical transmitters and receivers are located within boxes that are distributed across the airframe. Due to tight physical space requirements, the boxes are packaged in remote, hard to reach locations. Therefore, an optical transmitter with the capability to autonomously perform OTDR would be a great benefit to maintainers of the aircraft.

The above presented problem(s) is also found in parallel fiber optic components. Parallel fiber optic components operate on multiple individual fibers in parallel. Each individual fiber is susceptible to a discontinuity. Parallel optic transmitters and transceivers transmit data over these multiple fibers connected into a single package. A transmitter or transceiver with an OTDR function embedded on each fiber channel would allow measurement of each of the individual fibers in the link.

Multiple modes of communication are achievable with fiber optic lines. For example, bi-directional data communications allow communication between two devices over a single fiber, thus reducing the need for a dedicated fiber communicating in each direction. Remote fiber sensing utilizes a laser to transmit light down an optical waveguide that is placed in a remote environment and measure properties back-reflected light. The remote environments can change the reflective properties of the fiber by various means, including: temperature, pressure, motion, humidity, and/or chemicals. Optical range finders utilize a laser to transmit a pulse into free space and measure the time-of-flight of the back-reflected light from an object.

As further described below, various exemplary embodiments address the means of providing bi-directional optical coupling between a single waveguide and a light emitter and detector devices. Such means can be applied to single-mode and multi-mode fiber waveguides. The means can be formed as a single component in a low-cost molding process, enabling: 1) a cost efficient method of implementing bi-directional coupling within the existing physical envelope of a transmitter component, and 2) a mechanically robust device capable of operating in harsh environmental conditions, such as shock and vibration.

Various exemplary embodiments can provide bi-directional coupling of light between an optical waveguide, an optical emitter and an optical detector. These embodiment(s) incorporate a patterned or coated surface that directs light from a light emitter into an optical waveguide and simultaneously directs light from the optical waveguide into an optical detector. The component can be designed to offer coupling efficiency greater than 70% between the light emitter and optical waveguide and simultaneously greater than 50% between the waveguide and the optical detector.

Various exemplary embodiments can also provide a component that will function with single wavelength communication systems and without preference to the polarization of the optical signals. The component can be manufactured using high precision molding techniques. Precision molding techniques can create plastic or glass features defined to accuracy of 5 microns or less. The component can contain elements to ease alignment to optical waveguides, light emitters and/or light detectors. These elements can be molded into the component along with the splitting surface and lenses associated with optical coupling. As one example, injection molding of thermoplastics can be used as a low-cost method for producing the component, lenses, etc. within fiber optic transmitters.

Various exemplary embodiments can provide a component that will withstand temperature cycles of −55 C to 100 C. Also, some embodiment(s) can allow for the integration of OTDR within a fiber optic transmitter to provide built-in-test without sacrificing transmitter performance requirements or physical size constraints. For example, this component can be implemented within a military grade fiber optic transmitter with an overall height constraint of 5 mm.

Also, a bi-directional coupling on each channel of a parallel (or multi-channel) transmitter can be realized. A common format for a parallel transmitter is the use of multiple fiber optic waveguides on a spacing of 250 microns. Various exemplary embodiments disclosed here offer bi-directional coupling on each of the multiple waveguides within a parallel transmitter.

In one exemplary embodiment, the optical waveguide is a multimode fiber. The light source can be a vertical cavity surface emitting laser (VCSEL) and the light detector can be a PIN detector, which are mounted on a transparent substrate. Of course, other light sources and detector types may be utilized according to design preference. A surface that splits the light is molded in a formable material and is aligned to lenses for coupling light to the multimode fiber and for coupling to the light source(s) and the detector devices(s). Nearly all of the light from the source device strikes one or more surfaces oriented at an angle to the light path. The light from these angled surfaces is reflected toward the multimode fiber due to the total internal reflection within the formable material. The light from the multimode fiber strikes the splitting surface and passes through some regions within the light path. These regions are large enough to allow more than half of the light to pass through and ultimately onto the detector. Also molded into this component can be an alignment guide pin for aligning the multimode fiber to a lens on the component and features to mount a reflector to direct light from the splitting surface into the detector. The light source and detector devices are electronically connected to circuitry that performs the OTDR function.

Bi-directional coupling efficiency is a concern for most electro-optic engineers. For example, let EW represents the fraction of optical energy coupled between the emitter (E) and waveguide (W), and WD represents the fraction of optical energy coupled between the waveguide (W) and detector (D) in the reverse direction. U.S. Pat. No. 7,341,384, by Chan et al, discloses a method of bi-directionally coupling using an angle polished fiber as the splitting surface. In this configuration, the best possible combination of coupling efficiencies, EW and WD, is unity (EW+WD=1). For example, if angle polish is 48 degrees, then 50% of the light from the emitter will be directed to the fiber and 50% of the returning light from the fiber will be directed to the detector. This method relies on the time-invariance property of optics, meaning the system works the same way for light propagation in either direction. Another drawback of this approach is that the manufacturing method does not allow for the single step integration of coupling lenses. Lens devices are needed in certain circumstances to aid in coupling. For example, when the fiber cannot be placed physically close to the light emitter or light detector, a lens system forms a relay system between the devices. The lenses would need to be manufactured separately and assembled as separate pieces within the transmitter package.

Conventional bi-directional coupling methods cannot achieve coupling with EW+WD>1 for a single wavelength without control of the polarization. A well known method of coupling light of achieving EW+WD>1 with polarized light uses a polarizing beam splitter (PBS). A light emitter with a known linear polarization can be oriented so that nearly all of the light reflects at an angle of 90 degrees from the PBS. If this light passes through a quarter wave plate (QWP), the light becomes circularly polarized. If this light were then directed back through the same QWP and the PBS, the polarization would again be linearly polarized in an orientation that nearly all the light would pass directly through the PBS without reflecting at 90 degrees and could be captured by a detector. However, the need to control polarization entails the requirement of devices such as QWPs, which add to the complexity and cost, as well as introduce optical loss.

As detailed herein, this disclosure describes exemplary embodiments with very high combined efficiency of the coupling in both directions: 1) between the emitter and waveguide and 2) between the waveguide and detector. Various exemplary embodiments allow bi-directional coupling with EW+WD>1. This property can be achieved without regard to the optical wavelength or polarization of the optical energy. Therefore, the exemplary embodiments can be utilized in products such as VCSEL-based data communication over multimode fibers, since a single wavelength is commonly utilized and the polarization of the optical energy is not controlled.

Configuration

FIG. 1 is diagram of an exemplary system embodiment 1 for coupling light between light emitter 3 and waveguide 2 using splitting surface 6 to turn light (shown lines 16) toward waveguide 2, and using this splitting surface 6 to pass light from waveguide 2 to reflector 7. The reflector 7 turns light toward detector 4. Structure 5 is disposed between the light emitter 3 and waveguide 2 and contains lens 9 to couple light (shown by arrows 14) from light emitter 3 to splitting surface 6, lens 8 to couple light between waveguide 2 and splitting surface 6, structure surface 12 to mount reflector 7, lens 10 to couple light (shown by arrows 15) between splitting surface 6 and light detector 4, and stand-off 13 to control the distance between lens elements 9 and 10 and light emitter 3 and light detector 4, respectively. An optional transparent carrier 11 can provide mechanical support for light emitter 3, light detector 4 and structure 5.

Figure 2:
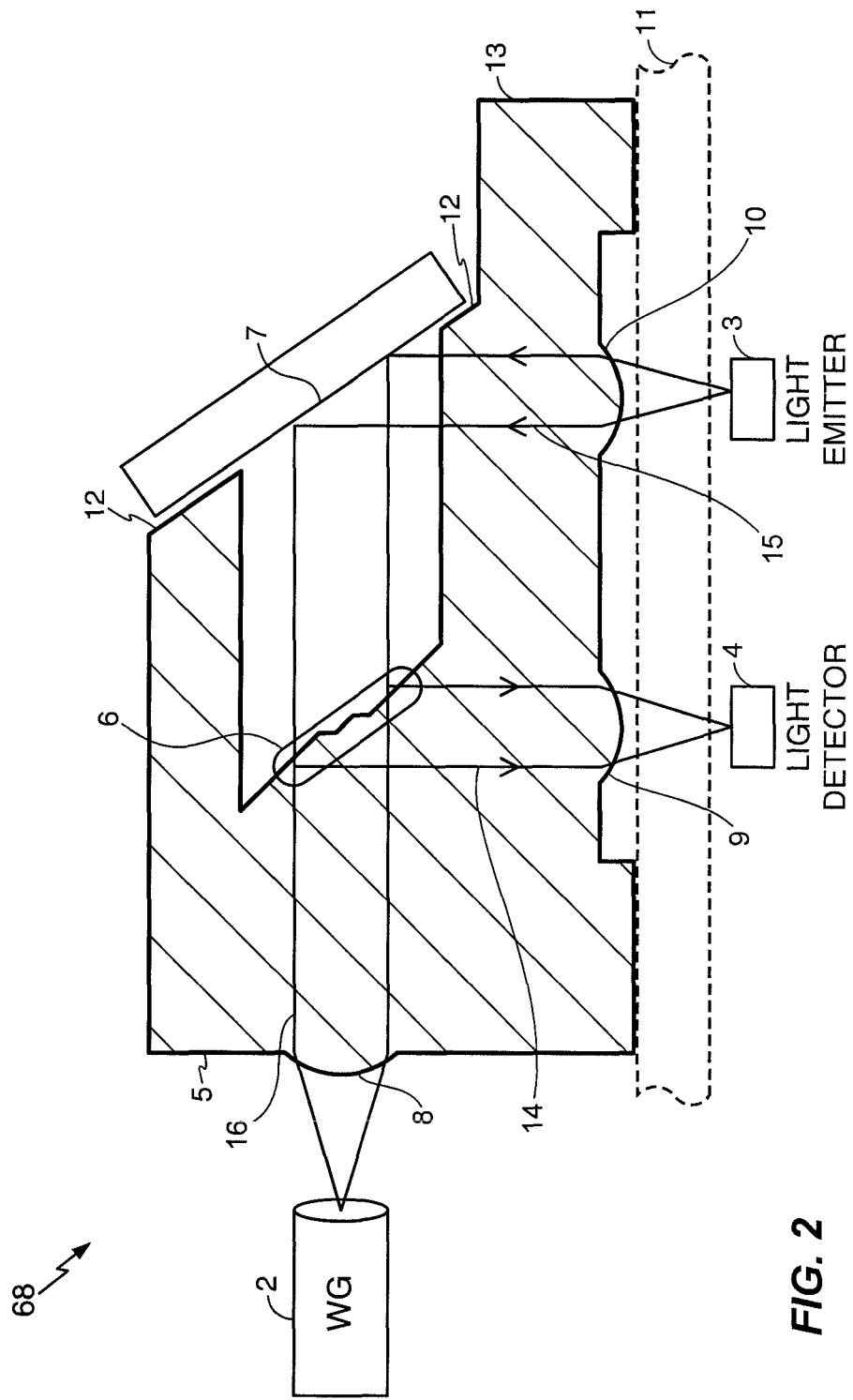
FIG. 2 is a diagram of an embodiment showing coupling light between a light detector and waveguide using a first surface turn light toward a detector, and using this first surface to pass light from the light emitter to the waveguide. The second surface reflector turns the light toward the waveguide.

FIG. 2 is a diagram of another exemplary system embodiment 68 for coupling light (shown by arrows 15) between light emitter 3 and waveguide 2 using reflector 7 to turn the light toward waveguide 2 and direct the light through splitting surface 6 and into waveguide 2. Light from waveguide 2 (shown by lines 16) is turned toward detector 4 by splitting surface 6 and directed to light detector 4. Structure 5 is disposed between the light emitter 3 and waveguide 2 and contains lens 10 to couple light from light emitter 3 to splitting surface 6, lens 8 to couple light between waveguide 2 and splitting surface 6, surface 12 to mount reflector 7, lens 9 to couple light (shown by arrows 14) between splitting surface 6 and light detector 4, and stand-off 13 to control the distance between lens elements 10 and 9 and light emitter 3 and light detector 4, respectively. An optional transparent carrier 11 can provide mechanical support for light emitter 3, light detector 4 and structure 5.

Figure 3:
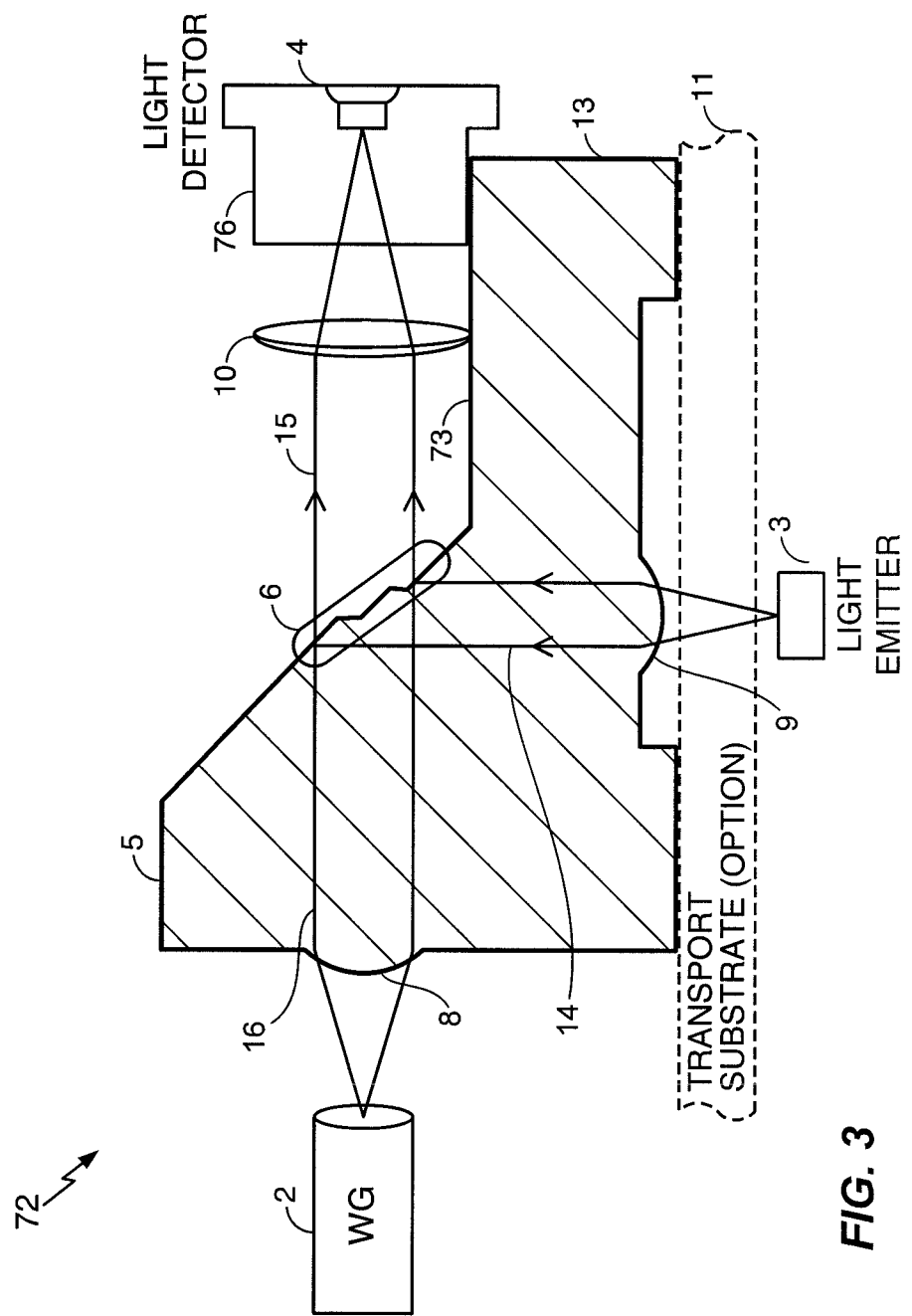
FIG. 3 is a diagram of an embodiment showing coupling light between a light emitter and waveguide using a first surface turn light toward the waveguide, and using this first surface to pass light from the waveguide to a light detector.

FIG. 3 is a diagram of another system embodiment 72 for coupling light between a light emitter 3 and waveguide 2 using splitting surface 6 to turn light toward waveguide 2, and using this splitting surface 6 to pass light from waveguide 2 to light detector 4. Structure 5 is disposed between the light emitter 3 and waveguide 2 and contains lens 9 to couple light (shown by arrows 14) from light emitter 3 to splitting surface 6, lens 8 to couple light (shown by lines 16) between waveguide 2 and splitting surface 6, surface 73 to mount light detector assembly 76, lens 10 to couple light (shown by arrows 15) between splitting surface 6 and light detector 4, and stand-off 13 to control the distance between lens element 9 and light emitter 3. An optional transparent carrier 11 can provide mechanical support for light emitter 3 and structure 5.

Figure 4:
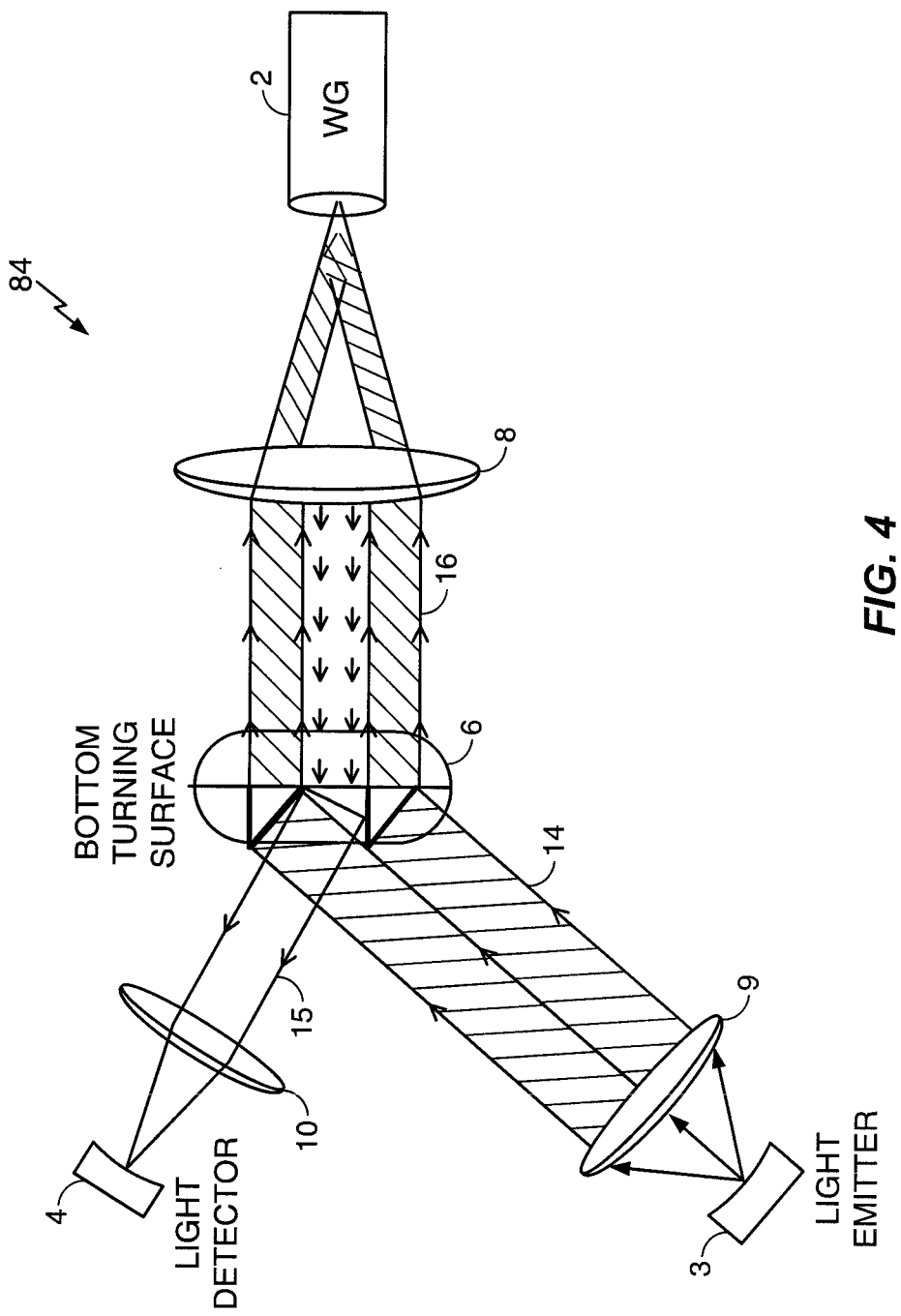
FIG. 4 is a diagram of an embodiment showing a transmissive system for bi-directionally coupling light between a light emitter and detector and a waveguide.

FIG. 4 is diagram of another exemplary system embodiment 84 that couples light from light emitter 3 through lens 9 onto splitting surface 6. The light from light emitter 3 passes through lens 9 and travels (shown by arrows 14) through splitting surface 6 to lens 8 via arrows 16 and is coupled to waveguide 2. Light from waveguide 2 is coupled to splitting surface 6 using lens 8. This light passes through splitting surface 6 and is coupled (shown by arrows 15) into light detector 4 using lens 10.

Figure 5:
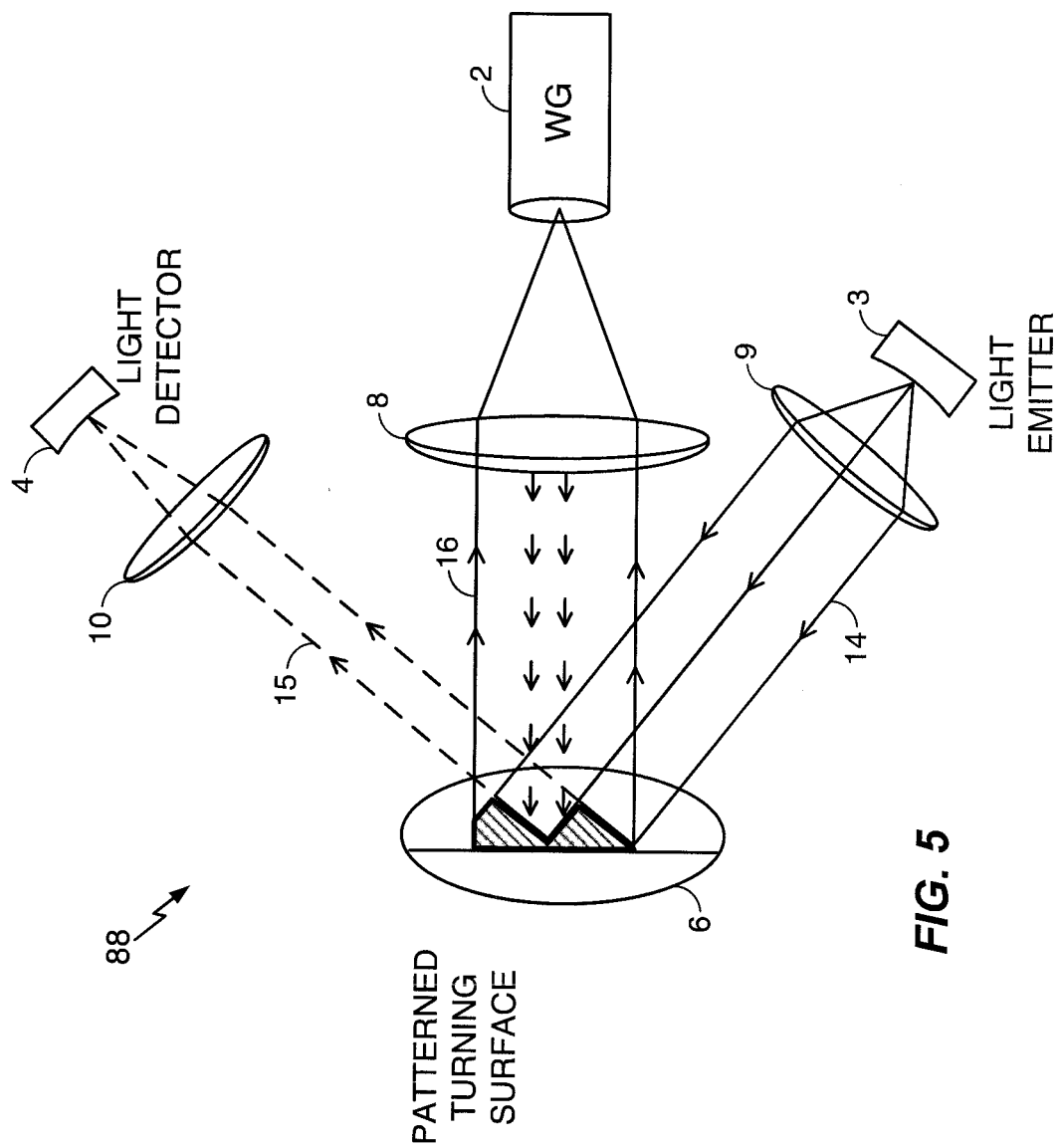
FIG. 5 is a diagram of an embodiment showing a reflective system for bi-directionally coupling light between a light emitter and detector and a waveguide.

FIG. 5 is a diagram of another exemplary system embodiment 88 that couples light from light emitter 3 via arrows 14 through lens 9 onto splitting surface 6. The light reflects (shown by arrows 16) from splitting surface 6 and is coupled into waveguide 2 with the aid of lens 8. Light from waveguide 2 is coupled to splitting surface 6 using lens 8. This light reflects (shown by arrows 15) from splitting surface 6 and is coupled into light detector 4 using lens 10.

FIG. 6A is a diagram of an exemplary embodiment 92 using multi-step structural interfacial surface for splitting light. The light path 93 contains sub-paths A, B and C that reflect from surface areas 96, 98 and 100, respectively, and form a light beam containing sub-paths A', B', and C', respectively, in the region of light path 95. Light path 95 contains sub-paths V, W, X, Y, and Z that strike surface areas 96, 97, 98, 99, and 100 respectively. Light sub-paths W and Y pass through surface areas 97 and 99, respectively, to form sub-paths W' and Y' within light path 94. For light from light path 93, the light reflects from the splitting surfaces 96, 98 and 100 in a 2-D pattern 102 with regions A', B' and C'. For light from light path 95, the light strikes the splitting surfaces 96, 97, 98, 99 and 100 in a 2-D pattern 101 with regions W', and Y'.

FIG. 6B is a diagram of another exemplary embodiment 106 using a single-step structural interfacial surface for splitting light. The light path 110 contains sub-paths A and B that reflect from surface areas 122 and 124, respectively, and form a light beam path containing sub-paths A' and B', respectively, in the region of light path 118. Light path 118 contains sub-paths X, Y, and Z that strike surface areas 122, 123, and 124, respectively. Light sub-path Y' passes through surface area 123 to form sub-path Y' within light path 114. Light from light path 110 reflects from the splitting surfaces 122 and 124 in a 2-D pattern 132 with regions A' and B'. Light from light path 118 strikes the splitting surfaces 122, 123 and 124 in a 2-D pattern 128 with region Y'.

FIG. 6C is a diagram of another exemplary embodiment 136 using a reflection mode structural interfacial surface for splitting light. The light path 140 contains sub-paths A and B that reflect from the surface areas 155 and 153, respectively, and form a light beam containing sub-paths A' and B', respectively, in the region of light path 148. Light path 148 contains sub-paths X, Y, and Z that strike surface areas 153, 154, and 155, respectively. Light sub-path Y reflects from surface area 154 to form sub-paths Y' within light path 144.

FIG. 6D is a diagram of an exemplary embodiment 160 using a transmission mode structural interfacial surface for splitting light. The light path 164 contains sub-paths A and B that pass through surface areas 176 and 178, respectively, and form a light beam containing sub-paths A' and B', respectively, in the region of light path 172. Light path 172 contains sub-paths X, Y, and Z that strike surface areas 176, 177, and 178 respectively. Light sub-path Y passes through the surface area 177 to form sub-paths Y' within light path 168.

Figure 6F:
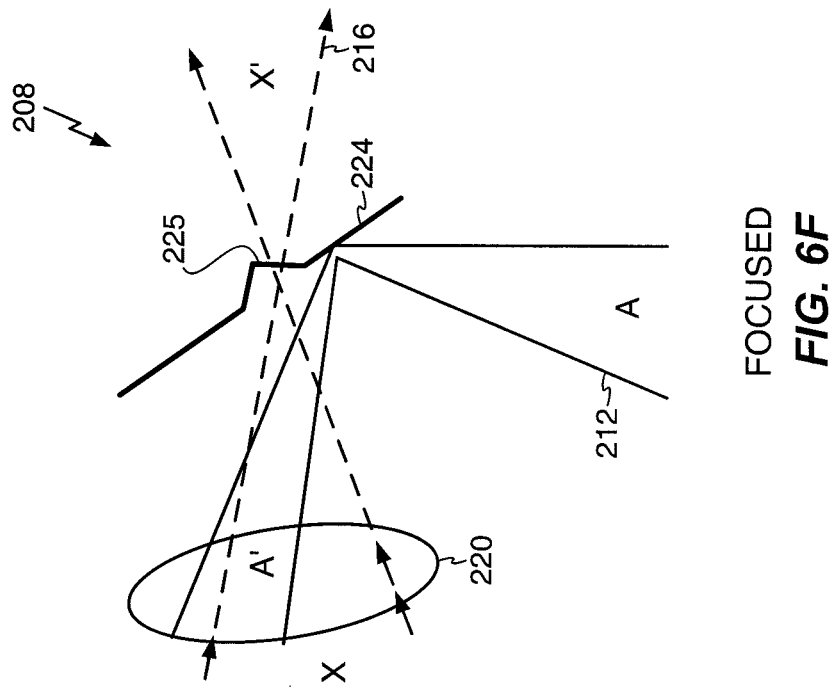
Figure 6E:
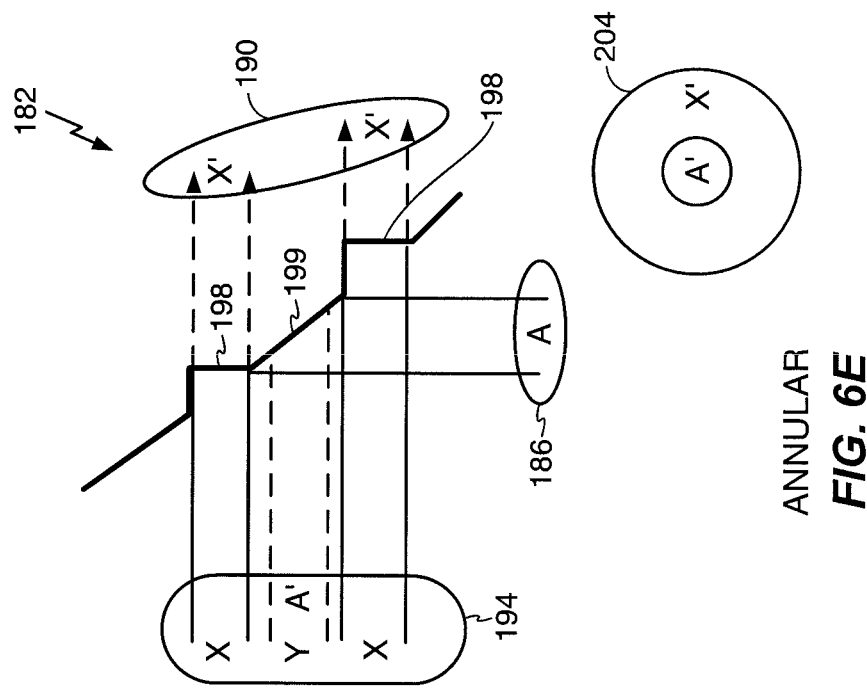

FIG. 6E is a diagram of another exemplary embodiment 182 using an annular aperture splitting structural interfacial surface for splitting light. The light path 186 contains sub-path A which reflects from the surface areas 199 to form a light beam containing sub-path A' in the region of light path 194. Light path 194 contains sub-paths X, Y, and Z that strike surface areas 198 and 199. Light sub-path X passes through the surface area 198 to form sub-paths X' within light path 190. If viewed from the perspective of the light path 194, the light reflects from splitting surface 199 in a 2-D pattern of region A' and light passes through the splitting surface 198 in a 2-D pattern of region X', as shown by the annular regions 204.

FIG. 6F is a diagram of another exemplary embodiment 208 using a structural interfacial surface for splitting light that is converging to a point. The light path 212 contains sub-path A which reflects from surface areas 224 to form a light beam containing sub-path A' in the region of light path 220. Light path 220 contains sub-path X that passes through surface areas 225 to form sub-path X' within light path 216.

FIG. 6G is a diagram of an exemplary embodiment 230 using a structural interfacial surface for splitting light that uses a divisional lens. The light path 234 contains sub-paths A and B which are generated by a lens 252 that creates a plurality of sub-paths. Sub-paths A and B reflect from surfaces 246 and 248, respectively and form light path 242 with sub-paths A' and B' resulting in the beam profile 254. The light path 242 with sub-path X passes through surface area 247 to form sub-path X' within light path 238.

FIG. 6H is a diagram of an exemplary embodiment 260 using a structural interfacial surface for splitting light that uses a semi-reflective surface 276. The light path 264 contains sub-path A which partially reflects from surface 276 into sub-path A' within light path 272. Light path 272 contains sub-path X which partially transmits through surface 276 into X' within light path 268. Semi-reflective surface 276 can be a half-silvered mirror, if so desired.

Figure 6I:
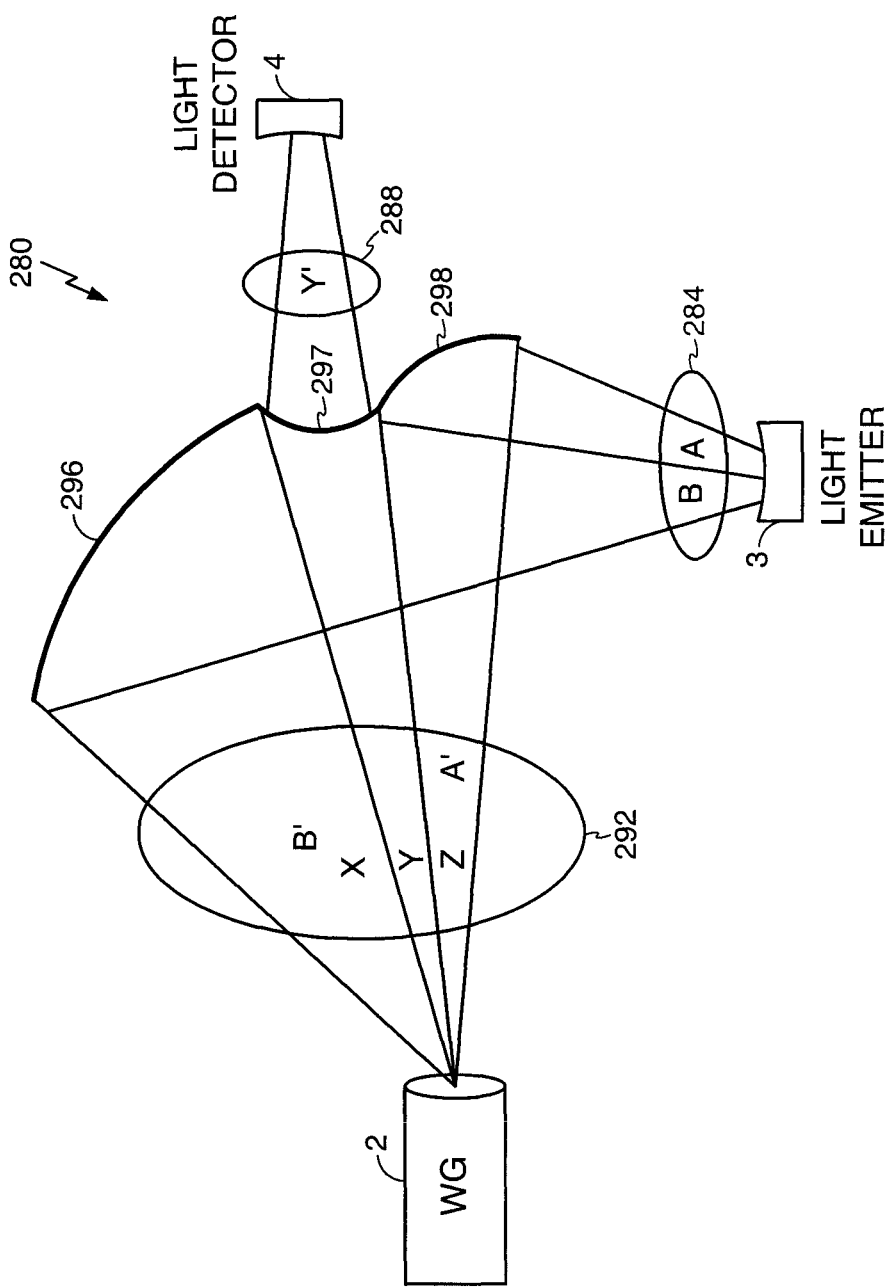

FIG. 6I is a diagram of an exemplary embodiment 280 using a structural interfacial surface for splitting light utilizing curved focusing surfaces. The light path 284 containing sub-paths A and B is generated from an optical source 3. Sub-paths A and B are reflected and focused by surfaces 298 and 296, respectively to form sub-paths A' and B' within light path 292. Light path 292 contains sub-paths X, Y and Z generated from a wave guide 2. Sub-path Y passes through surface area 297 to form sub-path Y' within beam path 288 and couples to a light detector 4.

Figure 7:
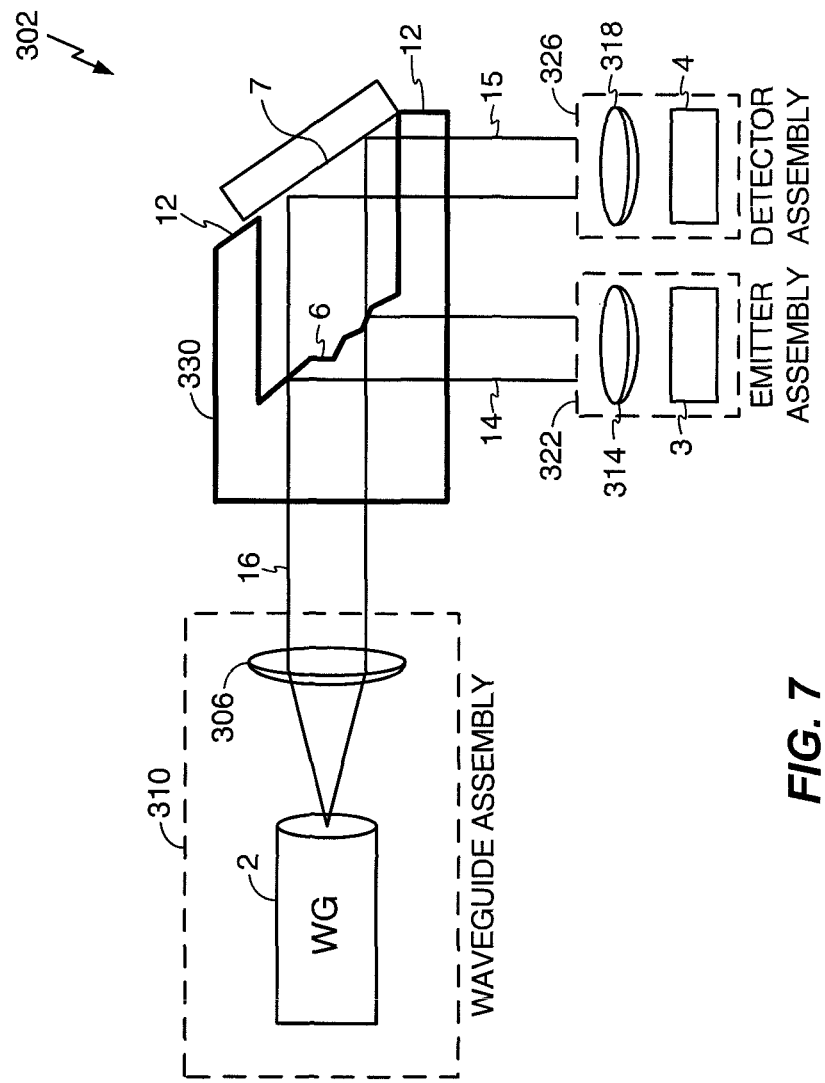
FIG. 7 is a diagram of an embodiment showing a bi-directional coupling system constructed with individual lens components aligned to light emitter, light detector and waveguide.

FIG. 7 is a diagram of an exemplary system embodiment 302 that couples light from a light emitting assembly 322 to a waveguide assembly 310 using a light splitting assembly 330. This exemplary system also couples light from a waveguide assembly 310 to a detector assembly 326 using light splitting assembly 330. The light emitting assembly 322 contains a light emitting device 3 coupled to the light splitting assembly 330 using a lens 314. The waveguide sub-assembly 310 contains an optical waveguide 2 coupled to the light splitting sub-assembly 330 using a lens 306. The detector assembly 326 contains an optical detector 4 coupled to the light splitting assembly 330 using a lens 318. The light splitting assembly 330 has an optical splitting surface 6 which reflects light from the light emitting assembly 322 on light path 14 toward the waveguide assembly 310 on light path 16. The splitting surface 6 also directs a portion of the light from the waveguide assembly 310 on light path 16 to a reflecting surface 7 which directs the light onto light path 15 toward the detector assembly 326. The light splitting assembly 330 has features 12 that align the reflecting surface 7 to the splitting surface 6.

Figure 8:
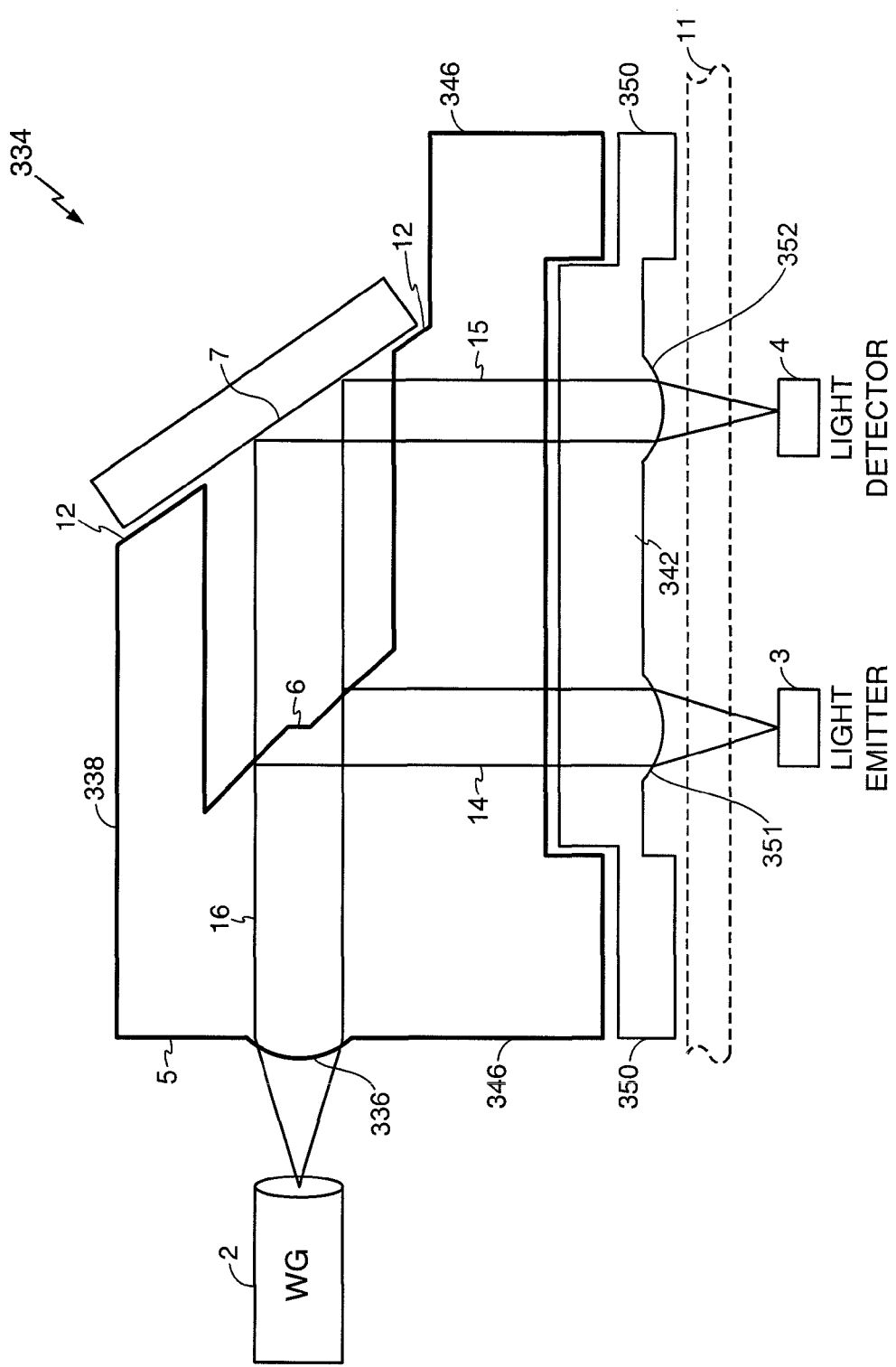
FIG. 8 is a diagram of an embodiment showing a bi-directional coupling system constructed as two sub-assemblies containing lens elements.

FIG. 8 is a diagram of an exemplary system embodiment 334 that couples light from a light emitter 3 to optical waveguide 2 and from waveguide 2 to light detector 4 using an optical waveguide coupling assembly 338 and a light emitter and detector coupling component 342. The optical waveguide coupling assembly 338 contains a lens 336 for coupling light between the optical waveguide 2 and the splitting surface 6 on light path 16. The optical waveguide coupling assembly 338 contains features 12 for aligning the reflecting surface 7 to the splitting surface 6. The optical waveguide coupling assembly 338 contains features 346 for mechanical alignment to the light emitter and detector component 342. The light emitter and detector component 342 contains lenses 351 and 352 for coupling to the splitting surface 6 and reflecting surface 7, respectively. The light emitter and detector component 342 contains standoff features 350 to set the distance between the light emitter 3 and the light detector 4 and the lenses 351 and 352. An optional transparent carrier 11 can provide mechanical support for the light emitter 3, light detector 4 and the light emitter and detector coupling component 342.

Figure 9A:
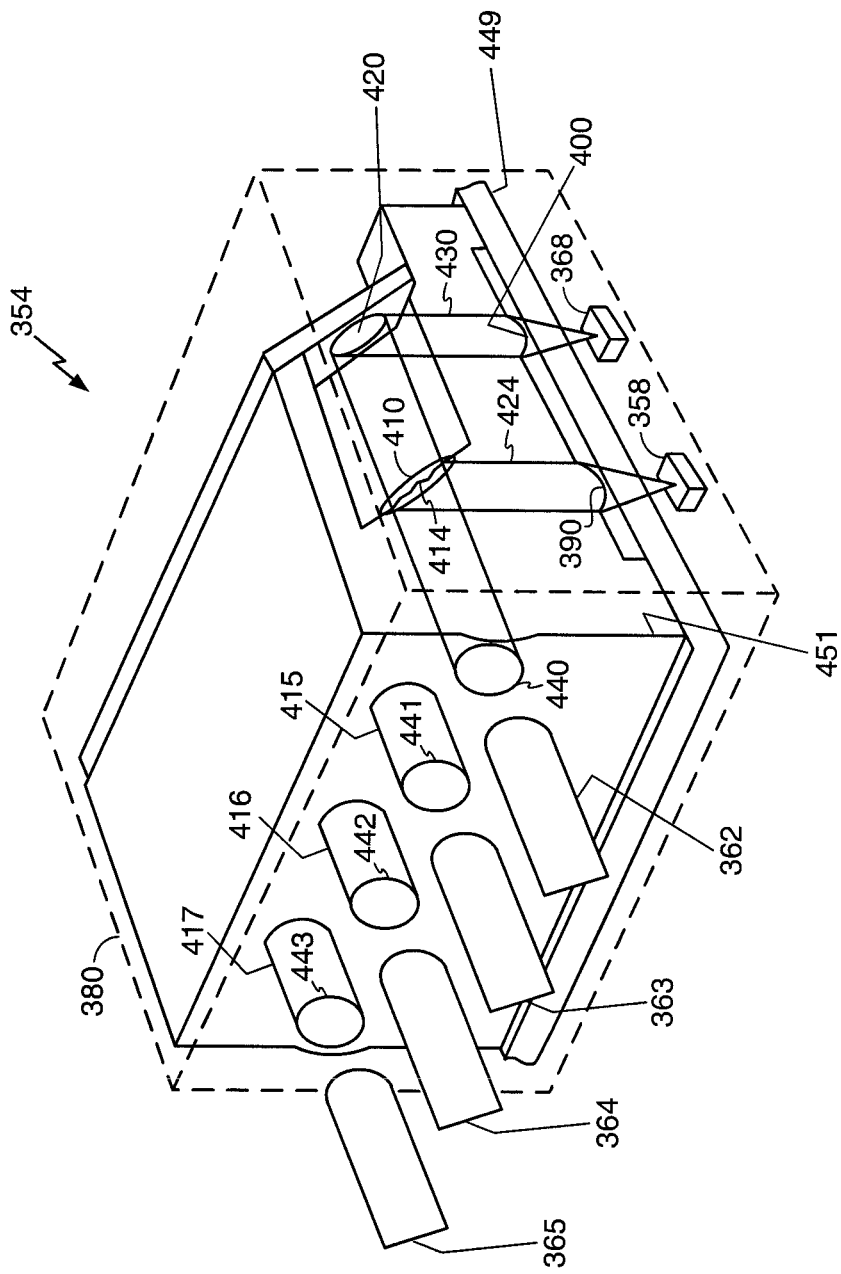
FIGS. 9A-B are diagrams of embodiments showing a bi-directional coupling system operating on multiple, independent light channels in an array.
Figure 9B:
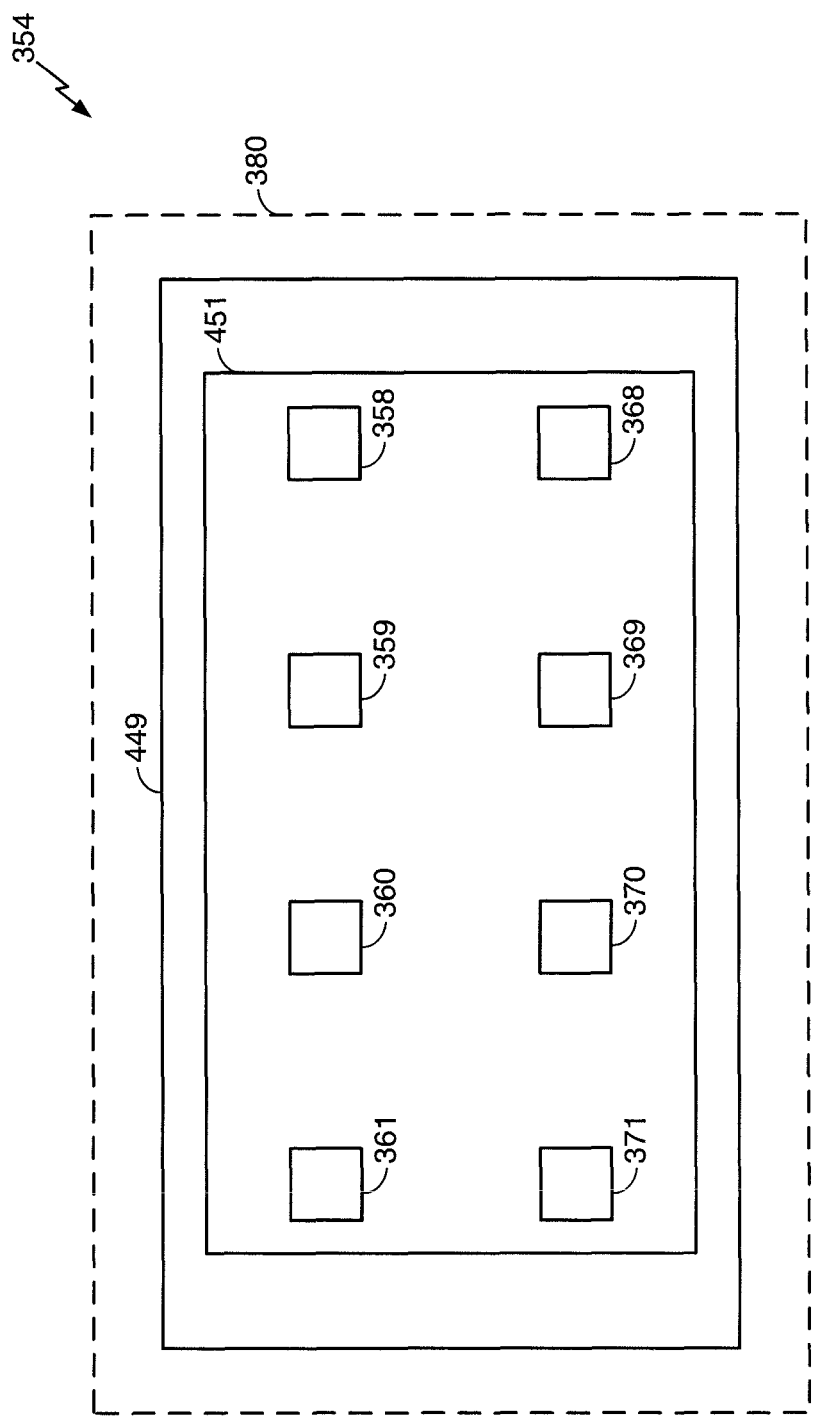

FIGS. 9A-B are diagrams showing a perspective view and plan view of an exemplary system embodiment 354 that couples light from an array of N light emitters 358, 359, . . . 358+(N−1) to an array of optical waveguides 362, 363, . . . 362+(N−1), and from an array of optical waveguides 362, 363, . . . 362+(N−1) to an array of detectors 368, 369, . . . 368+(N−1). This system contains an array of lenses 440, 441, . . . 440+(N−1) that couples light from the optical waveguides 362, 363, . . . 362+(N−1) to the beam splitting surface 410, which contains regions of light splitting elements 414, 415, . . . 414+(N−1). The light splitting elements 414, 415, . . . 414+(N−1) direct light from the light emitter coupling lenses 390, 391, . . . 390+(N−1) toward the array of lenses 440, 441, . . . 440+(N−1) and directs light from the array of lenses 440, 441, . . . 440+(N−1) toward a reflecting surface 420. The reflecting surface 420 directs light toward the array of detector coupling lenses 400, 401, . . . 400+(N−1). A bi-directional coupling assembly 380 is mounted on a transparent carrier 449. A single structure 451 contains the array of lenses 440, 441, . . . 440+(N−1), splitting surface 410, the light emitter coupling lenses 390, 391, . . . 390+(N−1) and the array of detector coupling lenses 400, 401, . . . 400+(N−1).

Figure 10:
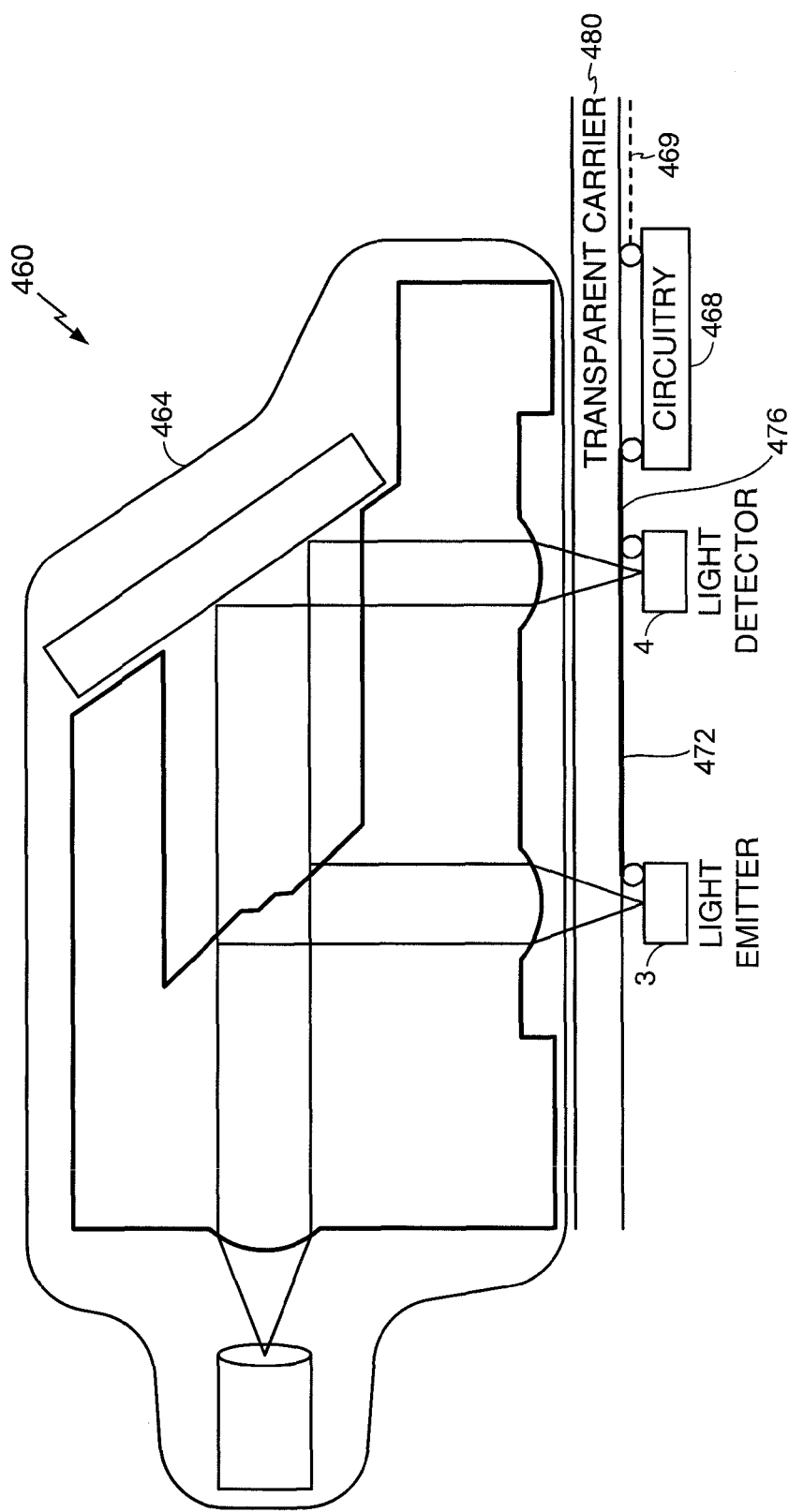
FIG. 10 is a diagram of an embodiment showing a bi-directional coupling system combined with an optically transparent carrier that provides electrical connectivity between circuitry and light emitter and light detector.

FIG. 10 is a diagram of an exemplary system embodiment 460 for performing coupling between a bi-directional coupling assembly 464 and a light emitter 3 and light detector 4 which are electrically connected via electrical paths 472 and 476, respectively, to an integrated circuit 468. The integrated circuit 468 is mounted on a "bottom-side" of transparent carrier 480, which contains the electrical paths 472 and 476. Additional circuitry 469 could be formed on the transparent carrier 480.

Figure 11:
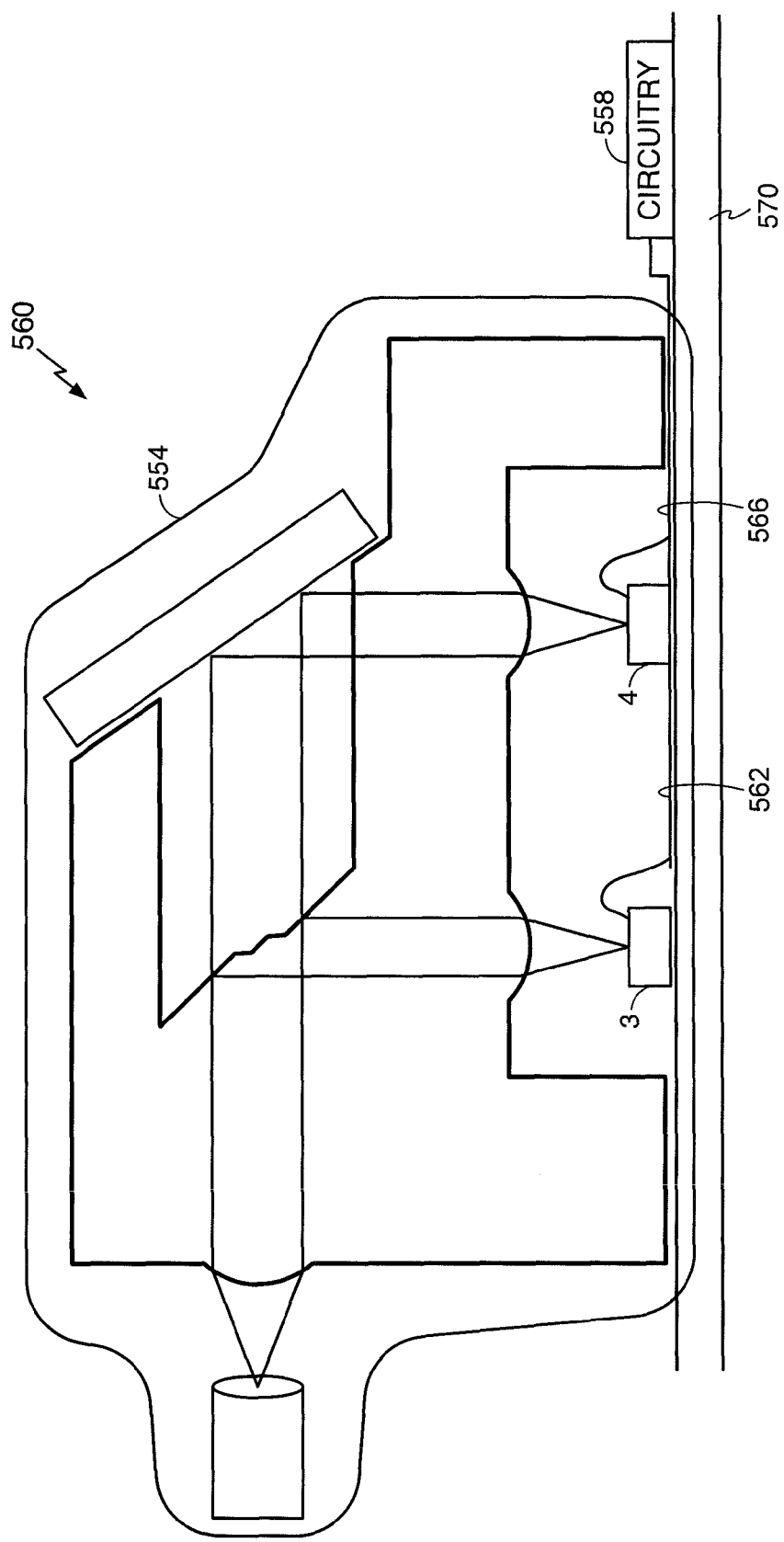
FIG. 11 is a diagram of an embodiment showing a bi-directional coupling system combined with electronic circuitry in communication with light emitter and light detector.

FIG. 11 is a diagram of an exemplary system embodiment 560 for performing coupling between a bi-directional coupling assembly 554 and a light emitter 3 and light detector 4 which are electrically connected via electrical paths 562 and 566, respectively, to an integrated circuit 558. The circuitry is mounted on a "top-side" of carrier 570, which contains the electrical paths 562 and 566.

Figure 12:
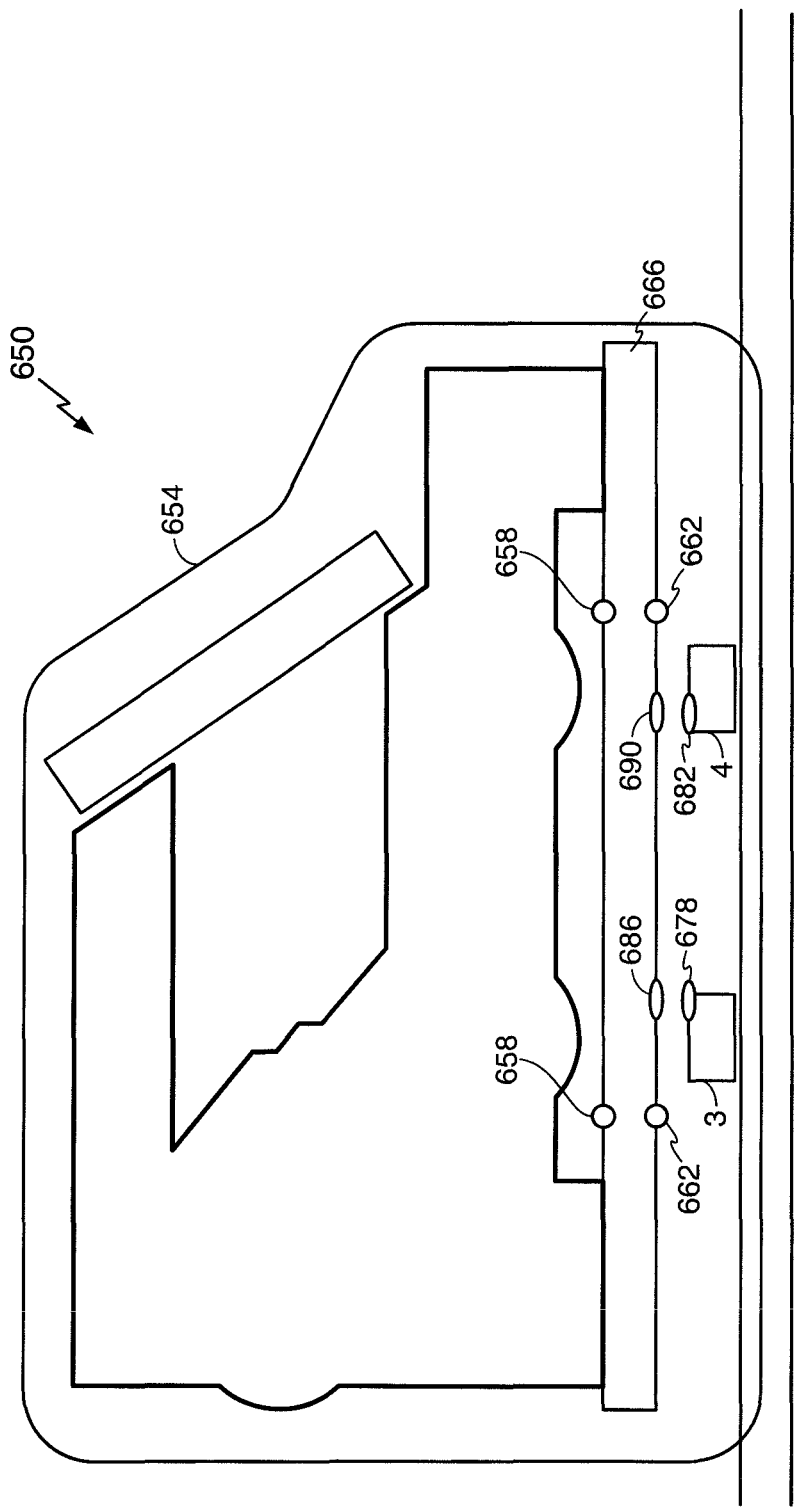
FIG. 12 is a diagram of an embodiment showing a bi-directional coupling system containing features that aid in aligning light emitters and light detectors to a transparent carrier and features that aid in aligning a bi-directional coupling element to a transparent carrier.

FIG. 12 is a diagram of an exemplary system embodiment 650 showing bi-directional coupling assembly 654 that contains features 658 that are in alignment with features 662 formed in a transparent carrier 666. The transparent carrier 666 contains a feature 686 that is in alignment to feature 678 formed on the light emitter 3. The transparent carrier 666 contains feature 690 that is in alignment to feature 682 on the light detector 4.

Figure 13:
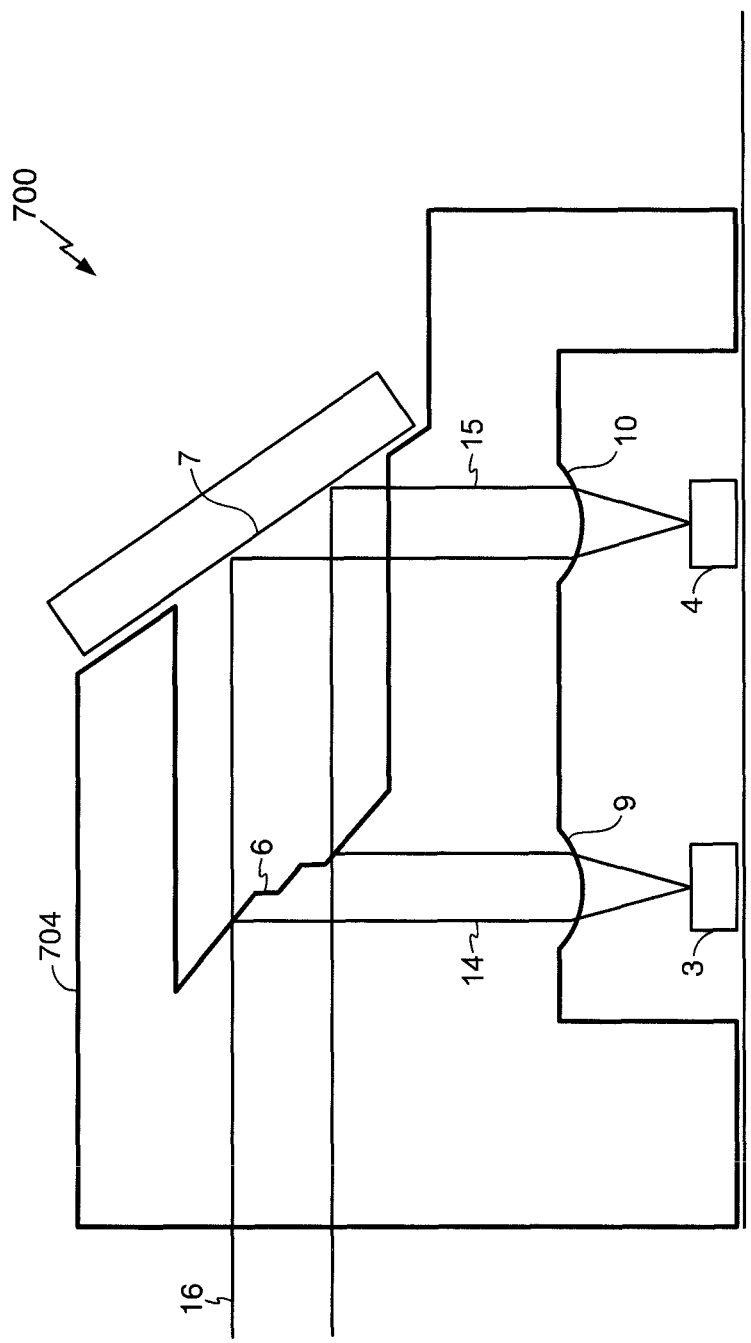
FIG. 13 is a diagram of an embodiment showing a bi-directional coupling system for applications that do not use an optical waveguide.

FIG. 13 is a diagram of an exemplary system embodiment 700 showing a bi-directional coupling assembly 704 that is suitable for applications that do not use an optical waveguide. The light emitter 3 is coupled to the splitting surface 7 with a lens 9 in light path 14. The splitting surface 6 reflects the light into light path 16 exiting the assembly 704. Light entering the assembly 704 on light path 16 is partially passed through splitting surface 6 to reflecting surface 7. Light from surface 7 is coupled into the light detector 4 using lens 10.

Figure 14A:
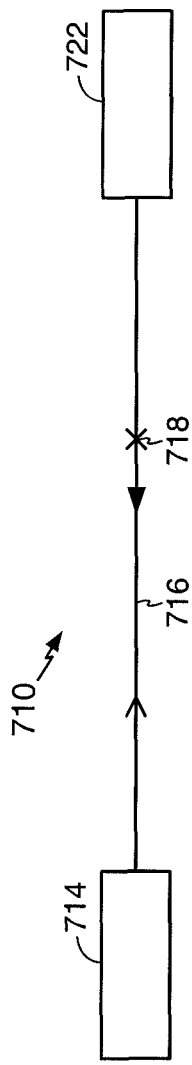
FIGS. 14A-D are diagrams of embodiments showing a bi-directional coupling system.

FIG. 14A is an exemplary embodiment 710 of a communication link implementing OTDR. The transmitter 714 contains an OTDR function and is sending information on an optical waveguide 716 to an optical receiver 722. The optical waveguide 716 contains one or more optical discontinuities 718. Using time-of-flight calculation, the transmitter 714 can find the location of the discontinuity using OTDR methods.

Figure 14B:
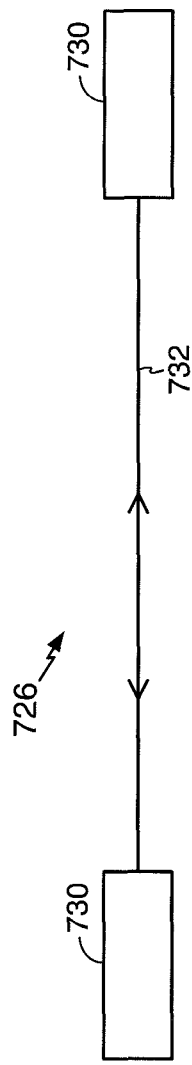
Figure 14C:
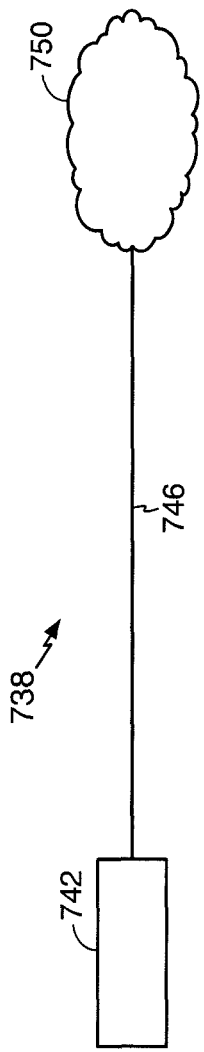

FIG. 14B is an exemplary embodiment 726 of a bi-directional communication link. The transceivers 730 are interconnected by a single optical waveguide 732. Information is optically transferred in both directions on this link FIG. 14C is an exemplary embodiment 738 of a remote optical waveguide sensor system. The illuminator and sensor component 742 is linked with an optical waveguide 746 to an environment 750 under test. The environment under test 750 varies the optical properties of the optical waveguide 746 which varies the optical reflectance of the waveguide 746.

Figure 14D:
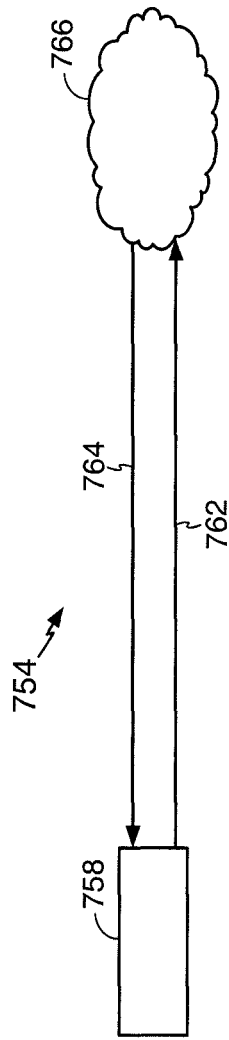

FIG. 14D is an exemplary embodiment 754 of a free space optical rangefinder. The illuminator and sensor component 758 transmits a light pulse through free space on light path 762. The light is reflected from a remote object 766 and some of the light returns to the illuminator and sensor component 758 on light path 764. Using time-of-flight calculation, the system 754 can determine the distance of the remote object 766 from the illuminator and sensor 758.

Figure 15:
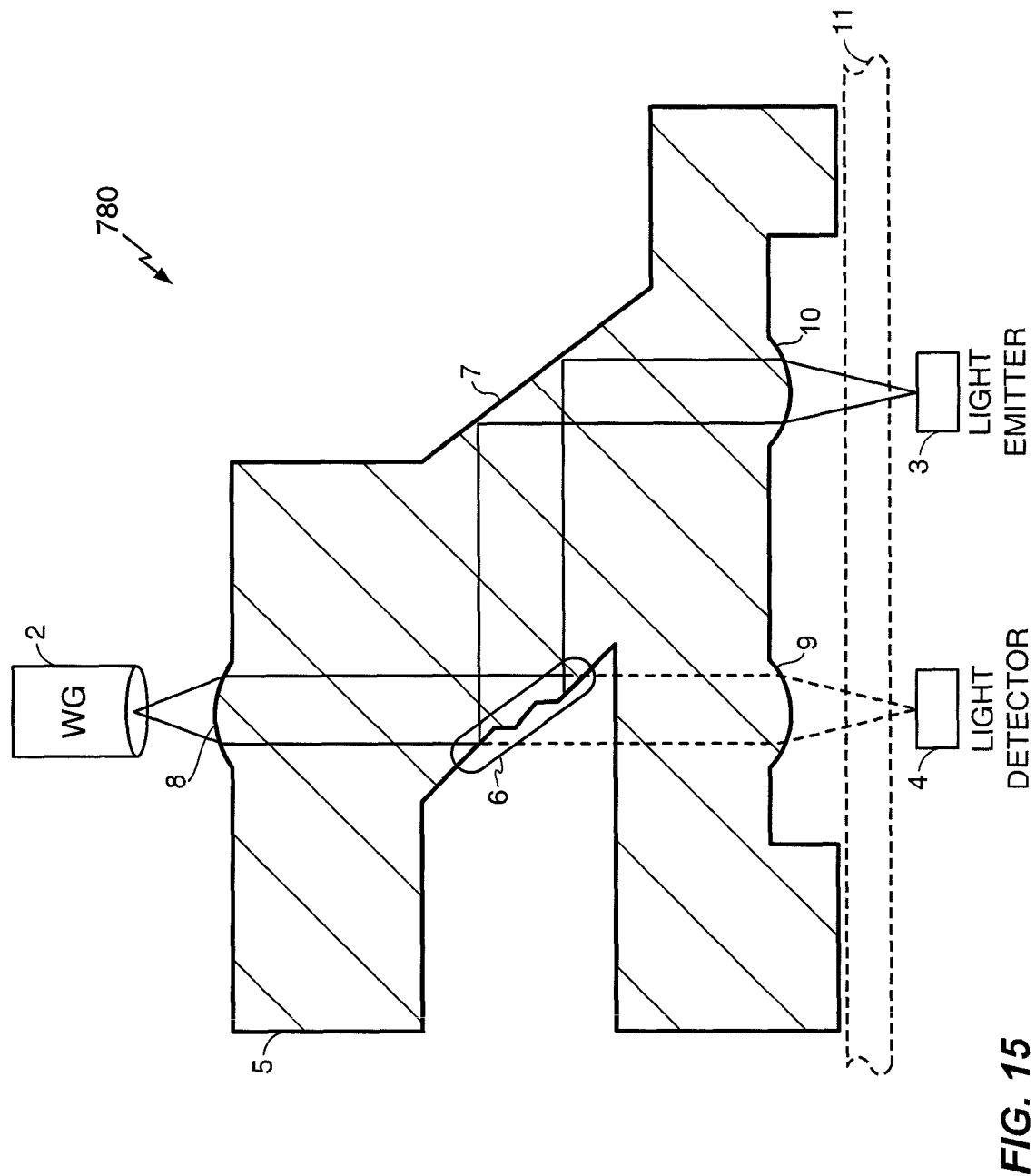
FIG. 15 is a diagram showing an embodiment 780 with an integrated reflector and collinear waveguide-to-light emitter configuration.

FIG. 15 is an exemplary embodiment 780 wherein the waveguide 2 and lens 8 are in line with the splitting surface 6, lens 9 and light detector 4. In this embodiment, the reflector 7 may be integral to the structure 5, thus allowing light from the splitting surface 6 to be directed to lens 10 and light emitter 3. Optionally shown is a transparent substrate 11 disposed between structure 5 and the light detector 4/light emitter 3.

As is apparent from the various embodiments shown, multiple configurations and arrangements may be devised, once the general principles having been explained herein are understood. Accordingly, many changes may be made to the embodiments described herein without departing from the spirit and scope of this disclosure.

Additionally, it should be understood that many additional changes in the details, materials, steps and arrangement of parts, which have been herein described and illustrated to explain the nature of the invention, may be made by those skilled in the art within the principle and scope of the invention as expressed in the appended claims.

What is claimed is:

1. A device for transmitting and reflecting light between a plurality of lenses, comprising:
   a multi-sided transparent body having a detector-emitter side, a waveguide side, a reflector side, and an indent with a light splitting surface formed as one piece with the body at an interior end of the indent;
   a first lens formed as one piece with the body at the detector-emitter side of the body;
   a second lens formed as one piece with the body at the waveguide side of the body;
   a third lens formed as one piece with the body at the detector-emitter side of the body, wherein light from the second lens is partially reflected by the light splitting surface to the detector-emitter side of the body and partially passed by the light splitting surface; and
   upper and lower reflector-supporting angled surfaces formed as one piece with the body located adjacent to and at an exterior end of the indent; and
   a reflector disposed onto the angled surfaces, closing the indent, directing the partially passed light from the light splitting surface to the third lens and directing light from the third lens to the light splitting surface.

2. The device of claim 1, further comprising:
   a standoff formed as one piece with the body to the detector-emitter side of the body and providing a gap between at least the first and third lens from an end of the standoff.

3. The device of claim 1, further comprising a transparent substrate having a lens side and an opposite non-lens side, disposed exterior to the body, wherein the lens side of the substrate is substantially adjacent to the first and third lens.

4. The device of claim 3, further comprising:
a light emitter disposed on the non-lens side of the substrate, and in alignment with at least one of the first and third lens;
a light emitter electrical contact disposed on the light emitter;
a first contact point disposed on the non-lens side of the substrate, and aligned in contact with the light emitter electrical contact;
a light detector disposed on the non-lens of the substrate, and in alignment with at least one of the first and third lens;
a light detector electrical contact disposed on the light detector; and
a second contact point disposed on the non-lens side of the substrate, and aligned in contact with the light detector electrical contact.

5. The device of claim 4, further comprising a first lens electrical contact point on the lens side of the substrate and a light emitter/detector electrical contact point on the non-lens side of the substrate.

6. A method for transmitting and reflecting light between a plurality of integral lenses, comprising:
forming a multi-sided transparent body with an indent therein, the body having a detector-emitter side, a waveguide side, and a reflector side;
forming as one piece with the body a light splitting surface at an interior end of the indent, capable of passing and reflecting split light;
forming as one piece with the body a first lens at the detector-emitter side of the body;
forming as one piece with the body a second lens at the waveguide side of the body, wherein the first lens and second lens are disposed in a reflected split light path of each other;
forming as one piece with the body a third lens to the detector-emitter side of the body, wherein light from the second lens is partially reflected by the light splitting surface to the detector-emitter side of the body and partially passed by the light splitting surface;
forming as one piece with the body a plurality of reflector supporting angled surfaces adjacent to and at an exterior end of the indent;
attaching a reflector onto the angled surfaces, closing the indent, the reflector reflecting light from the third lens to the light splitting surface and reflecting light from the light splitting surface to the third lens;
positioning a light emitter in line with the first lens,
positioning a light detector in line with the third lens;
positioning a waveguide in line with the second lens;
positioning a reflector on the angled surface;
emitting light from the light emitter to be directed to the waveguide via the light splitting surface; and
receiving waveguide light passing through the light splitting surface and reflected from the reflector to the light detector.

7. The method of claim 6, wherein time domain reflectometry is performed by measuring a time delay between the emitted and the received light.

8. A method for transmitting and reflecting light between a plurality of lenses, comprising:
forming a multi-sided transparent body having a first and second indent therein, the body having a detector-emitter side, a waveguide side, and a reflector side;
forming as one piece with the body a light splitting surface at an interior end of the first indent, capable of passing and reflecting split light;
forming as one piece with the body a first lens at the detector-emitter side of the body;
forming as one piece with the body a second lens at the waveguide side of the body, wherein the first lens and second lens are disposed in a reflected split light path of each other;
forming as one piece with the body a third lens at the detector-emitter side of the body, wherein light from the second lens is partially reflected by the light splitting surface to the detector-emitter side of the body and partially passed by the light splitting surface;
forming as one piece with the body a plurality of reflector supporting angled surfaces adjacent to and at an exterior end of the indent;
attaching a reflector onto the angled surfaces, closing the indent, the reflector reflecting light from the third lens to the light splitting surface and reflecting light from the light splitting surface to the third lens;
positioning a light emitter within the second indent and in line with the first lens,
positioning a light detector within the second indent and in line with the third lens;
positioning a waveguide in line with the second lens;
positioning a reflector on the angled surface;
emitting light from the light emitter to be directed to the waveguide via the light splitting surface; and
receiving waveguide light passing through the light splitting surface and reflected from the reflector to the light detector.

9. The method of claim 8, wherein time domain reflectometry is performed by measuring a time delay between the emitted and the received light.

10. A device for transmitting and reflecting light between a plurality of lenses, comprising:
means for light path manipulation having an indent, a detector-emitter side, a waveguide side, and a reflector side;
means for splitting light formed as one piece with the means for light path manipulation disposed at an interior end of the indent;
first means for focusing light formed as one piece with the means for light path manipulation disposed at the detector-emitter side of the means for light path manipulation;
second means for focusing light formed as one piece with the means for light path manipulation disposed at the waveguide side of the means for light path manipulation;
third means for focusing light formed as one piece with the means for light path manipulation disposed at the detector-emitter side of the means for light path manipulation, wherein light from the second means for focusing is partially reflected by the means for splitting light to the detector-emitter side of the means for light path manipulation, and partially passed by the means for light splitting;
means for supporting a reflector disposed adjacent to and at an exterior end of the indent;
a reflector disposed onto the means for supporting, closing the indent, directing the partially passed light from the means for splitting light to the third means for focusing light and directing light from the third means for focusing light to the means for splitting light.

11. The device of claim 10, further comprising:
means for standing off formed as one piece with the body to the detector-emitter side of the means for light path manipulation and for providing a gap between at least the first and third means for focusing light from an end of the means for standing off.

12. The device of claim 11, further comprising a transparent substrate disposed substantially approximate to the first and third means for focusing light.

13. A device for transmitting and reflecting light between a plurality of lenses, comprising:
- a multi-sided transparent body having a substrate side, a waveguide side, and light splitting surface side formed as one piece with the body;
- a first indent disposed in the light splitting side of the body;
- a second indent disposed in the substrate side of the body;
- a first and third lens formed as one piece with the body at an interior end of the second indent;
- a second lens formed as one piece with the body at the waveguide side of the body;
- a light splitting surface formed as one piece with the body at the light splitting surface side of the body, positioned to reflect a portion of light from the first lens to the second lens and pass a portion of light from the second lens to the third lens;
- upper and lower reflector-supporting angled surfaces formed as one piece with the body, located adjacent to and at an exterior end of the indent;
- a reflector disposed onto the angled surfaces, closing the indent, directing the passed portion of light from the second lens to the third lens;
- a light emitter disposed below the first lens and within the second indent; and
- a light detector disposed below the third lens and within the second indent.

* * * * *